(12) United States Patent
Tang et al.

(10) Patent No.: US 10,406,154 B2
(45) Date of Patent: *Sep. 10, 2019

(54) TRANSDERMAL DOSAGE FORM

(71) Applicant: Clexio Biosciences Ltd., Jerusalem, IL (US)

(72) Inventors: John Tang, Basking Ridge, NJ (US); Prashant Patel, Parsippany, NJ (US); Bhavik Patel, Jersey City, NJ (US); Longchun Yu, Nanuet, NY (US)

(73) Assignee: Clexio Biosciences Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,009

(22) Filed: Jul. 2, 2018

(65) Prior Publication Data

US 2018/0303827 A1 Oct. 25, 2018

Related U.S. Application Data

(63) Continuation of application No. 14/757,954, filed on Dec. 23, 2015, now Pat. No. 10,010,543.

(60) Provisional application No. 62/096,393, filed on Dec. 23, 2014.

(51) Int. Cl.
*A61K 9/70* (2006.01)
*A61K 31/485* (2006.01)
*A61K 31/4468* (2006.01)
*A61K 9/00* (2006.01)

(52) U.S. Cl.
CPC .......... *A61K 31/485* (2013.01); *A61K 9/0014* (2013.01); *A61K 9/7092* (2013.01); *A61K 31/4468* (2013.01)

(58) Field of Classification Search
None
See application file for complete search history.

(56) References Cited

U.S. PATENT DOCUMENTS

| | | | |
|---|---|---|---|
| 4,539,256 A | 9/1985 | Shipman | |
| 4,693,776 A | 9/1987 | Krampe et al. | |
| 5,147,538 A | 9/1992 | Wright et al. | |
| 5,149,538 A | 9/1992 | Granger et al. | |
| 5,236,714 A | 8/1993 | Lee et al. | |
| 5,474,783 A | 12/1995 | Miranda et al. | |
| 5,585,111 A | 12/1996 | Peterson | |
| 5,985,317 A | 11/1999 | Venkateshwaran et al. | |
| 7,182,955 B2 | 2/2007 | Hart et al. | |
| 8,440,220 B2 | 5/2013 | Gale et al. | |
| 8,475,837 B2 | 7/2013 | Anderson et al. | |
| 8,481,560 B2 | 7/2013 | Stinchcomb et al. | |
| 8,747,889 B2 | 6/2014 | Gale et al. | |
| 8,778,382 B2 | 7/2014 | Howard et al. | |
| 8,790,689 B2 | 7/2014 | Howard et al. | |
| 9,226,902 B2 | 1/2016 | Tang | |
| 2002/0119187 A1 | 8/2002 | Cantor et al. | |
| 2003/0026829 A1 | 2/2003 | Venkatraman et al. | |
| 2004/0033253 A1 | 2/2004 | Shevchuk et al. | |
| 2004/0109886 A1 | 6/2004 | Rigby | |
| 2004/0126323 A1 | 7/2004 | Shevchuk et al. | |
| 2004/0219195 A1 | 11/2004 | Hart et al. | |
| 2004/0241218 A1 | 12/2004 | Tavares et al. | |
| 2005/0095279 A1 | 5/2005 | Gale et al. | |
| 2006/0257460 A1 | 11/2006 | Jansen et al. | |
| 2007/0065365 A1 | 3/2007 | Kugelmann et al. | |
| 2008/0008747 A1 | 1/2008 | Royds | |
| 2008/0020028 A1 | 1/2008 | Shevchuk et al. | |
| 2008/0022698 A1 | 1/2008 | Hobbs | |
| 2008/0226698 A1 | 9/2008 | Tang et al. | |
| 2008/0233178 A1 | 9/2008 | Reidenberg et al. | |
| 2009/0246265 A1 | 10/2009 | Stinchcomb et al. | |
| 2010/0076198 A1 | 3/2010 | Nichols | |
| 2011/0150766 A1 | 6/2011 | Royds | |
| 2011/0245783 A1 | 10/2011 | Stinchcomb et al. | |
| 2011/0269727 A1 | 11/2011 | Toledano | |
| 2017/0209429 A1 | 7/2017 | Stinchcomb et al. | |

FOREIGN PATENT DOCUMENTS

CN 102068697 A 5/2011
WO 2011/120070 A1 10/2011

OTHER PUBLICATIONS

Trescot et al., Opioids in the Management of Chronic Non-Cancer Pain: An Update of American Society of the Interventional Pain Physicians' (ASIPP) Guidelines, Pain Physician, 11:S5-S62, Mar. 2008.
Thomas, Unusual Fentanyl Patch Administration, The American Journal of Forensic Medicine and Pathology, 29(2):162-163, Jun. 2008.
Tharp et al., Fatal Intravenous Fentanyl Abuse Four Cases Involving Extraction of Fentanyl From Transdermal Patches, The American Journal of Forensic Medicine and Pathology, 25(2):178-181, Jun. 2004.
Stanos et al. Strategies to Reduce the Tampering and Subsequent Abuse of Long-Acting Opioids: Potential Risks and Benefits of Formulations with Physical or Pharmacologic Deterrents to Tampering, Mayo Clin. Proc., 87(7): 683-694, Jul. 2012.
Raffa et al., Designing Opioids That Deter Abuse, Hindawi Publishing Corporation, Pain Research and Treatment, 10 Pages, 2012.
Prosser et al., Complications of Oral Exposure to Fentanyl Transdermal Delivery System Patches, J. Med. Toxicol., 6:443-447, Jun. 2010.
Moon et al., Fentanyl Intoxication Caused by Abuse of Transdermal Fentanyl, The Journal of Emergency Medicine, 40(1): 37-40, Jan. 2011.
Liappas, Oral Transmucosal Abuse of Transdermal Fentanyl, Journal of Psychopharmacology, 18(2):277-280, Jun. 2004.
Kuhlman et al., Fentanyl Use, Misuse, and Abuse: A Summary of 23 Postmortem Cases, Journal of Analytical Toxicology, 27:499-504, Oct. 2013.

(Continued)

*Primary Examiner* — Susan T Tran
(74) *Attorney, Agent, or Firm* — BakerHostetler

(57) ABSTRACT

The disclosure generally relates to tamper-resistant transdermal dosage forms. The dosage forms can comprise an active agent and more than one antagonist reservoir.

27 Claims, 13 Drawing Sheets

(56) References Cited

OTHER PUBLICATIONS

Katz et al., Tampering with Prescription Opioids: Nature and Extent of the Problem, Health Consequences, and Solutions, The American Journal of Drug and Alcohol Abuse, Early Online: 1-13, Jul. 2011.
Jumbelic, Deaths with Transdermal Fentanyl Patches, The American Journal of Forensic Medicine and Pathology, 31(1):18-21, Mar. 2010.
Flannagan, et al., Fentanyl Patches Left on Dead Bodies—Potential Source of Drug for Abusers, Journal of Forensic Sciences, JFSCA, 41(2):320-321, Mar. 1996.
Duragesic (Registerd) (fentanyl transdermal system), Physician's Desk Reference, 56th Edition, Ed.: Medical Economics Company, pp. 1786-1789, Jan. 2002.
Carson et al., A Fatality Involving an Unusual Route of Fentanyl Delivery: Chewing and Aspirating the Transdermal Patch, Legal Medicine, 12:157-159, Mar. 2010.
Cai et al. Development and Evaluation of a Tampering resistant Transdermal Fentanyl Patch, International Journal of Pharmaceutics, 488(1-2): 102-107, Jul. 2015.
Abuse-Resistant Transdermal Dosage Form, Jun. 24, 2008, Hart, John, 30 pages.
Abuse-Resistant Transdermal Dosage Form, Jun. 24, 2008, Hart, John.

TRANSDERMAL DOSAGE FORM

CROSS REFERENCE TO RELATED APPLICATIONS

This application is a continuation of U.S. application Ser. No. 14/757,954, filed Dec. 23, 2015, which claims the benefit of the priority of U.S. Provisional Patent Application No. 62/096,393, filed Dec. 23, 2014, each of which is incorporated herein by reference herein for all purposes.

TECHNICAL FIELD

The present disclosure relates to transdermal dosage forms having reduced potential for abuse. In particular, the disclosure relates to a system of transdermal administration of an active agent or agonist for example fentanyl to a subject over an extended period of time, wherein when subject to abuse, the system is capable of providing an adverse agent: active agent release ratio sufficient to prevent or discourage the abuse of the active agent. The present disclosure further relates to tamper-resistant transdermal dosage forms comprising: an active agent and a barrier which separates an antagonist in the form of a salt from the antagonist in base form.

BACKGROUND

Pain is the most frequent reported symptom and is a common clinical problem confronting the clinician. Opioids have long been recognized as one of the most effective treatments of pain whether for treating or preventing cancer pain, central pain, myocardial infarction pain, pancreatic pain, colic pain, post-operative pain, headache pain, muscle pain, bone pain, and pain associated with intensive care. However, the US societal costs of prescription opioid abuse were estimated at more than $50 billion in 2007 and have only grown since.

Transdermal dosage forms offer a favorable route of administration by providing a method of administering sustained release of a drug for an extended period of time, while increasing patient compliance and decreasing extreme peaks and troughs in blood plasma. However, these dosage forms also contain large amounts of active agent and therefore also have a high potential for abuse.

There are many different approaches proposed to prevent abuse of transdermal patches. In particular, U.S. Pat. No. 5,236,714 discloses a dosage form comprising an abusable substance formulated with an antagonist for the abusable substance. U.S. Pat. No. 5,149,538 discloses a transdermal patch comprising an opioid and an antagonist for the opioid that is releasable upon ingestion or solvent immersion, wherein the two reservoirs are separated by an impermeable barrier. U.S. Pat. Nos. 8,747,889, 8,790,689, 7,182,955 each disclose a transdermal patch system comprising an opioid and an antagonist with different methods for the antagonist to leave the patch.

U.S. Pub. No. 20040126323 discloses a transdermal system with an opioid layer and an antagonist layer comprising antagonist salt and base form, both with or without a barrier separating the opioid and antagonist layer.

Although there seems to have been much research in the area, no one has been successful in bringing an abuse deterrent transdermal patch to the market even while the inadvertent misuse or abuse of transdermal dosage forms remains a significant health problem. Thus, there remains a need in the art for improved transdermal dosage forms that are effective for preventing abuse yet useful for delivering an active agent, such as an opioid or a pharmaceutically acceptable salt thereof.

SUMMARY

The present disclosure relates to an abuse deterrent transdermal dosage form wherein when contacted with skin, allows for the transdermal administration of an active agent, such as an opioid, but either (a) allows for the transdermal administration of only an amount of an antagonist that is ineffective for inhibiting the effect of the active agent, or (b) does not allow for the transdermal administration of the antagonist. However, if the transdermal dosage form of the disclosure is used to deliver an active agent via a route other than transdermal, such as buccal, nasal, oral, parenteral, rectal and/or vaginal, or if the transdermal dosage form is subjected to abuse or misuse, then the antagonist inhibits the effect of the active agent.

In one embodiment of the present disclosure, there is provided a transdermal dosage form having reduced potential for abuse comprising an active agent and more than one antagonist reservoir or source. In some embodiments, the transdermal dosage comprises a first antagonist component comprising an active agent and a first antagonist of the active agent, and a second antagonist component comprising a second antagonist of the active agent.

When an opioid is used as the active agent, release of the antagonist from one or both of the antagonist sources can inhibit the euphoric effect of the opioid. In some embodiments, the transdermal dosage form will inhibit the euphoric effect of an opioid if the device is used other than transdermally whether before or after the device is used by an animal or human for treating or preventing pain.

In one embodiment, the present disclosure is directed to an abuse deterrent transdermal dosage forms wherein the first and second antagonist are separated by a barrier. In a further embodiment, the first antagonist is in the form of a pharmaceutically acceptable salt and the second antagonist is in the form of a free base.

In another embodiment of the present disclosure, the first antagonist component has a proximal and distal surface; the second antagonist component is disposed distal to the first antagonist component and the barrier is interposed between the first and second antagonist components.

In another embodiment, the present disclosure is directed to transdermal dosage forms wherein the first antagonist component comprises a homogenous mixture of the active agent and the first antagonist or alternatively, wherein the active agent and the first antagonist are separated by one or more spacers.

In a more specific embodiment, the disclosure relates to a transdermal system for administering an active agent through the skin, the system having a reduced potential for abuse, comprising:
  (a) a first antagonist component comprising a first antagonist salt and an active agent in base form, wherein the active agent may be for example fentanyl or an analog thereof and the analog is selected from the group consisting of alfentanil, lofentanil, remifentanil, sufentanil and trefentanil;
  (b) a second antagonist component comprising a second antagonist in base form, optionally in amorphous base form, the antagonist being releasable from system upon being ingested or substantially immersed in a solvent, and further wherein the antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof; and (c) a barrier layer, said barrier layer separating said first and second antagonist components, said barrier layer being substantially impermeable to said active agents and/or excipients, wherein the release of the antagonist from the system when used transdermally is such that levels are sufficiently low that the active agent's effect is maintained for more than about two days or about three days; and the system provides release of the antagonist at a rate sufficient to provide an abuse limiting release rate ratio of the antagonist to the active agent when the dosage form is subject to abuse, e.g., upon transmucosal applications or substantial immersion of the system in the solvent.

The disclosure is further directed to a kit for treating pain in a patient, comprising: a) the transdermal-delivery device as disclosed above; and b) a printed set of instructions directing the use of the transdermal dosage form to treat pain.

The disclosure is further directed to methods for treating or preventing pain in an animal comprising contacting the skin of an animal in need thereof with any one or more of the transdermal dosage forms described above.

The disclosure is further directed to methods for reducing or preventing misuse of any one or more transdermal patches described above.

The present disclosure may be understood more fully by reference to the following figures, detailed description and examples, which are intended to exemplify non-limiting embodiments of the disclosure.

DETAILED DESCRIPTION OF ILLUSTRATIVE EMBODIMENTS

Definitions

Figure 1:
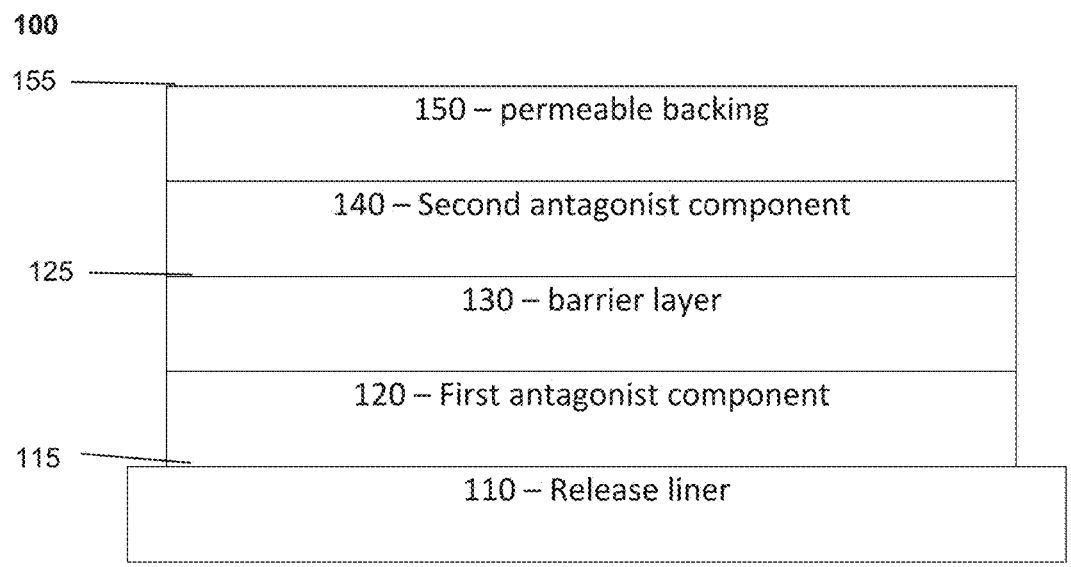
FIG. 1 is a schematic cross-section of a transdermal dosage system of the disclosure.

The phrases "transdermal dosage form" and "dosage form", as used herein, refer to any dosage form that, when contacted with a patient's skin for a sufficient period of time, can transdermally deliver an effective amount of any biologically active agent, such as a pharmaceutical agent, e.g., an opioid, through the patient's skin whether the type of transdermal dosage type is polymer-matrix-type, drug-in-adhesive-type, or other.

As used herein, the term "transmucosal" refers to buccal, nasally, sublingual, topical, rectal, and/or vaginal.

A "patient" or "animal" or "human" is a mammal, and includes, but is not limited to, a cow, monkey, horse, sheep, pig, chicken, turkey, quail, cat, dog, mouse, rat, rabbit, and guinea pig. In some embodiments, the "patient" or "animal" is a human.

As used herein the terms "dosage form" and "delivery device" are synonymous and interchangeable.

As used herein, the terms "abuse resistant" and "abuse deterrent" are synonymous and shall mean any transdermal dosage form that when misused, inhibits or deters the abuser from achieving the non-therapeutic effects sought from misuse of the composition, formulation or dosage form, such as opioid induced euphoria. Abuse or misuse shall mean any means including but not limited to being administered buccally, nasally, sublingually, parenterally, rectally, and/or vaginally to an animal.

As used herein, the phrase "active agent" refers to a pharmaceutical agent, therapeutic agent, drug, and/or agonist that causes a biological effect when absorbed in sufficient quantity into the blood stream of a patient. The active agent of the present disclosure unless otherwise indicated may be any drug substance that is capable of being abused. Many drugs have a potential for abuse, and include, for example, narcotics, such as morphine, fentanyl, codeine, sufentanil, and oxycodone; psychostimulants, such as amphetamine, methamphetamine, and methylphenidate; methoxy substituted amphetamines, such as 3,4-methylenedioxymethamphetamine (MDMA); and benzodiazepines, such as diazepam, oxazepam, and lorazepam. Examples include but are not limited to: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts or prodrugs thereof and mixtures of any two or more thereof. In some embodiments, the active agent is a narcotic such as fentanyl, alfentanil, carfentanil, lofentanil, remifentanil, sufentanil, trefentanil, and the like. In further embodiments, the active is fentanyl.

The term "biological effect" or "biological result" as used herein refers to a physical reaction in a patient. In some embodiments, the effect is analgesic, euphoria, respiratory, anti-depressive, or combinations thereof.

As used herein, the phrase "adverse agent" or "antagonist" refers to a pharmaceutical agent, drug, and/or antagonist that partially or completely prevents, negates, diminishes, delays or reverses at least one biological effect of the active agent present in the dosage form, e.g. euphoric effect, or produces one or more unpleasant physiological reactions, e.g., vomiting, nausea, diarrhea, bad taste, when absorbed in sufficient amount into the blood stream of a patient. When an opioid agonist is used as the active agent in the dosage form of the present disclosure, an opioid antagonist can be used as the adverse agent.

As used herein, the terms "opioid" or "opioid agonist" refer to an active agent which exhibits opium- or morphine-like properties when absorbed in sufficient amounts into the bloodstream of a patient. Opioid agonists bind, optionally stereo-specifically, to any one or more of several subspecies of opioid receptors and produce agonist activity.

As used herein, the phrase "opioid antagonist" refers to an adverse agent that either partially or completely prevents, negates, diminishes, delays or reverses at least one biological effect of an opioid agonist, e.g., euphoric effect, when absorbed in sufficient amounts into the blood stream of a patient.

The phrase "pharmaceutically acceptable salt," as used herein, is a salt formed from an acid and the basic nitrogen group of an opioid. In some embodiments, the salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, glubionate and pamoate (i.e., 1,1'-methylene-bis-(2-hydroxy-3-naphthoate)) salts. The term "pharmaceutically acceptable salt" also refers to a salt prepared from an opioid having an acidic functional group, such as a carboxylic acid or sulfonic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N, N,-dimethyl-N-(2-hydroxyethyl)amine, or tri-(2-hydroxyethyl)amine; N-methyl-D-glucamine; and amino acids such as arginine, lysine, and the like. The list is not meant to be exhaustive but merely illustrative as a person of ordinary skill in the art would appreciate that other salts of opioids may be prepared.

The active agent may be in any form which provides the desired biological effect. In addition to pharmaceutically acceptable salts, the active agent may be utilized in any solid state form such as amorphic or polymorphic form of the active agent. In some embodiments, the active agent is amorphous. In further embodiments, the active agent is crystalline. In further embodiments, the active agent includes the fentanyl polymorphs and amorphic forms described in U.S. Patent Publication No. 2010/0076198. The term "active agent" therefore encompasses all amorphic forms or polymorphic forms existing under any possible crystal morphology. In further embodiments, the active agent such as fentanyl is in the form of a base. In further embodiments, the active agent such as fentanyl base is in amorphous form when formulated with excipients in the final transdermal dosage form. In further embodiments, the antagonist such as Naltrexone is in salt form such as HCl. In further embodiments, the antagonist such as Naltrexone salt is in micronized form. In further embodiments, the micronized Naltrexone salt is maintained in crystalline form within the transdermal dosage form. In further embodiments, the transdermal dosage form comprises crystalline ionic antagonist such as Naltrexone salt, admixed with povidone and silicone. In further embodiments, the antagonist such as Naltrexone is in base form. In further embodiments, the antagonist such as Naltrexone base is in amorphous form when formulated with excipients in the final transdermal dosage form. In further embodiments, the transdermal dosage form comprises amorphous antagonist in base form such as Naltrexone base in povidone.

The active agent or salt thereof also may be in the form of a prodrug. Such prodrugs may include, without limitation, esters, carbamates sulfate, oximes, sulfamites, carbonates and other conventional "pro-drug" forms, which, when administered in such form, convert to the active agent in vivo. In some embodiment, the prodrugs are esters.

As used herein, the term "proximal" refers to the location of a component, when considered as a whole, at a position which is relatively near to a site for application of the transdermal dosage form. The term "proximal surface" refers to the surface of a component which, when considered as a whole, is relatively near to a site for application of the transdermal dosage form, as compared to other surfaces of the component. In certain embodiments, the proximal surface of a component can be either continuous or discontinuous.

As used herein, the term "distal" refers to the location of a component, when considered as a whole, at a position which is relatively distant from a site for application of the transdermal dosage form. The term "distal surface" refers to the surface of a component which, when considered as a whole, is relatively distant from a site for application of the transdermal dosage form, as compared to other surfaces of the component. In certain embodiments, the proximal surface of a component can be either continuous or discontinuous.

As used herein, a "component" refers to a layer, a stratum, a coating, a sheet, a film, a deposit, a sediment, a residue and/or a cover.

As used herein, a "spacer" is meant to include a strip, channel, pore, orifice, opening, void, gap, hole, crack and/or slit which to some degree provides a distance between two components. It may be made up of air, inactive ingredient, a barrier material or other.

As used herein, a "strip" is a formulation comprising either an active agent, antagonist or both in any desired geometry and may be either continuous or discontinuous and may be disposed in a pattern.

As used herein, a the "DURAGESIC™ fentanyl patch" is used interchangeably with "DUROGESIC™ fentanyl patch" and refers to a fentanyl patch.

The phrase "treatment of pain" or "treating pain," as used herein, includes amelioration of pain or the cessation of pain in an animal.

The phrase "prevention of pain" or "preventing pain," as used herein, includes the avoidance of the onset of pain in an animal.

As used herein, the phrase "dispersed" unless otherwise specified refers to dispersed, mixed, and/or dissolved either homogenously and/or heterogeneously.

As used herein, the phrase "component" refers to a layer, a stratum, a coating, a sheet, a film, a deposit, a sediment, a residue, and/or a cover. An "antagonist component" is a component comprising an antagonist. An antagonist component may or may not additional comprise an active agent. An "antagonist salt component" is a component comprising an antagonist salt. An "antagonist base component" is a component comprising an antagonist base. A "first antagonist component" is a component comprising an active agent and an antagonist.

As used herein, the term "opposed" as used with reference to two surfaces of a component refers to two surfaces which are generally facing in opposite directions regardless of whether one or both of the two surfaces are planar and/or parallel to each other.

As used herein, the terms "porous medium" and "porous material" are used interchangeably.

The term "reservoir" refers to a compartment or layer which contains one or more active or adverse agents. In some embodiments, a reservoir is a layer of the transdermal dosage system.

"Room temperature" refers to a typical indoor temperature. In some embodiments, room temperature is about 15 to about 25° C. In further embodiments, room temperature is about 20° C.

The modifier "about" or "substantially" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

The term "resistant to transdermal absorption" as used herein refers to the tendency of a compound to cross the epidermis layer. In some embodiments, resistant to transdermal absorption means that no amount of a compound discussed herein crosses the epidermis layer. In other embodiments, "resistant to transdermal absorption" includes a "biologically insignificant" or negligible amount.

The phase "biologically significant" refers to an amount of an active agent or antagonist described herein which results in one or more intended effect in a subject after administration. In some embodiments, the "biologically significant effect relates to a physiological symptom, an interaction between the active agent and/or antagonist and at least one component of the subject, among others. In other embodiments, the biologically significant effect is the binding or lack thereof of the active agent or agonist to a relevant receptor in a patient. In still further embodiments, the biologically significant effect is physically observed. In other embodiments, the biologically significant effect physically observed is less than the full effect of the active agent.

Alternatively, the phrase "biologically insignificant" refers to an amount of an active agent or antagonist described herein which results in no or less than an intended effect in a subject after administration. In some embodiments, the "biologically insignificant" effect relates to a physiological symptom, an interaction between the active agent and/or antagonist and at least one component of the subject, among others. In other embodiments, the biologically insignificant effect refers to the binding or lack thereof of the active agent or agonist to a relevant receptor in a patient. In still further embodiments, the biologically insignificant effect is not physically observed.

"Similar in effect" when used for comparing one or more compound refers to its ability to have a similar biological result, PK profile, PD profile, or combinations thereof. In some embodiments, "similar in effect" means bioequivalent as defined below. In other embodiments, the transdermal dosage system is similar in effect to the Duragesic® transdermal patch.

"Conformable" describes the ability of the transdermal dosage system to adapt in shape to the skin of the patient. In some embodiments, the patch is flexible. When applied as instructed, the transdermal dosage system moves as the skin of the patient moves. In some embodiments, the transdermal dosage system does not become displaced from the patient as the skin moves or shifts.

The term "bioequivalent" means that two products, i.e., transdermal patches, are expected to be the same. In some embodiments, "bioequivalent" means that, when two products are compared, there is no significant difference in the rate and/or extent to which the active agent becomes available at the site of drug action when administered at the same molar dose under similar conditions in an appropriately designed study." In further embodiments, transdermal bioequivalence to fentanyl may be determined as specified by the Food and Drug Administration using (FDA) bioequivalent with pharmacokinetic endpoints, adhesion studies, skin irritation studies, skin sensitization studies, or combinations thereof. See, e.g., the "Draft Guidance on Fentanyl", recommended May 2009, February 2010 provided by the FDA which is incorporated by reference. In other embodiments, the transdermal dosage system parallels the FDA PK standard of about 90% CI compared to the Duragesic® transdermal patch. In further embodiments, the transdermal dosage system has a mean cumulative adhesion score of less than or equal to 0 as defined in the "Draft Guidance on Fentanyl" provided by the FDA and discussed above. In still other embodiments, the transdermal dosage system has a mean cumulative irritation score of less than or equal to 0 as defined in the "Draft Guidance on Fentanyl" provided by the FDA and discussed above. In yet further embodiments, the transdermal dosage system has (a) one sensitizing response occurring at more than 24 hours after removal of the patch during the challenge phase, (b) the combined "dermal response" and "other effects" numeric score is at least 2 during the challenge phase, (c) the combined "dermal response" and "other effects" numeric scores obtained during the challenge phase are general higher than during the induction phase as defined in the "Draft Guidance on Fentanyl" provided by the FDA and discussed above.

The term "micronized" refers to particles wherein the particles are less than 10 μm in diameter. In other embodiments, D50 is less than about 10 μm or D10 is less than about 5 μm or D90 is less than about 30 μm. In further embodiments D50 is less than about 10 μm and D10 is less than about 5 μm and D90 is less than about 30 μm. A number of micronization techniques may be utilized to micronize one or more components of the transdermal dosage system including, without limitation, conventional jet mills. The particle size or particle size distribution may be determined using techniques in the art such as light diffraction methods such as devices of Malvern Instruments, mechanical sieve shaking method, or air jet sieve analyses.

DETAILED DESCRIPTION

The present disclosure is directed to a transdermal dosage system having reduced potential for abuse, without blocking the therapeutic or beneficial effects of the active agent when the system is applied to the skin. In particular, the system of the present disclosure provides for the controlled release of the antagonist at a rate sufficient to provide an abuse limiting release rate ratio of the antagonist to the active when the dosage form is subject to abuse whether via buccal administration or solvent extraction for injection, wherein the system provides for a substantially minimized/negligible skin sensitization response from antagonist exposure.

This transdermal dosage form, when contacted with an animal's skin, allows for the transdermal administration of an active such as an opioid, but either (a) allows for the transdermal administration of only an amount of an antagonist salt that is ineffective for inhibiting the analgesic effect of the opioid, or (b) does not allow for the transdermal administration of the antagonist. However, if the transdermal dosage form of the disclosure is used to deliver an opioid via a route other than transdermal, such as buccal, nasal, oral, parenteral, rectal and/or vaginal, or if the transdermal dosage form is subjected to abuse or misuse, then one or more sources the antagonist inhibit the euphoric effect of the opioid. In some embodiments, the transdermal dosage form will inhibit the euphoric effect of an opioid if the device is used other than transdermally whether before or after the device is used by an animal or human for treating or preventing pain.

The transdermal dosage form of the disclosure is also tamper-resistant in that if an abuser attempts to extract or separate an opioid from the transdermal dosage form, and self-administer the opioid via another route, such as, but not limited to, oral, parenteral, nasal, or buccal, rectal or vaginal, i.e., a route of administration that can result in a quick euphoric rush, the abuser would self-administer an amount of an antagonist along with the opioid, the amount of antagonist being effective to inhibit the euphoric effect of the opioid.

In another embodiment of the present disclosure, there is provided a transdermal dosage form having reduced potential for abuse comprising an antagonist to agonist weight ratio of more than 3:1. In another embodiment of the present disclosure, there is provided a transdermal dosage form having reduced potential for abuse comprising an antagonist to agonist weight ratio of about 4:1. The transdermal dosage form of the present disclosure would also have stability, adhesive properties as required by pharmaceutical regulatory approval.

In one embodiment of the present disclosure, there is provided a transdermal dosage form having reduced potential for abuse comprising an active agent and more than one antagonist reservoir or source.

In one embodiment, a transdermal dosage form comprises an active agent, a first antagonist component, and a second antagonist component. In one embodiment, the first antagonist component comprises an antagonist of the active agent in the form of a pharmaceutically acceptable salt, and the second antagonist component comprises an antagonist of the active agent in the form of a pharmaceutically acceptable base. In one embodiment, the first antagonist component comprises an antagonist of the active agent in the form of a pharmaceutically acceptable salt and the active agent and the second antagonist component comprises an antagonist of the active agent in the form of a pharmaceutically acceptable base. In one embodiment the present disclosure is directed to an abuse deterrent transdermal dosage forms wherein the first and second antagonist are separated by a barrier.

In another embodiment of the present disclosure, the transdermal dosage form the first antagonist component has a proximal and distal surface; the second antagonist component is disposed distal to the first antagonist component and the barrier is interposed between the first and second antagonist components. The dosage form may also include a backing layer located distal to the second antagonist component. In another embodiment, the backing layer is permeable to the second antagonist.

In another embodiment, the proximal surface of the first antagonist component has an area of about 5 to about 150 cm². In another embodiment, the surface area of the dosage form is about 5 to about 60 cm². In another embodiment, the surface area of the dosage form is about 25 to about 35 cm² or about 100 to about 125 cm². In another embodiment, the transdermal dosage form releases about 10 to about 100 mcg active agent per hour to skin. In another embodiment, the transdermal dosage form releases about 12.5, 25, 50, 75 or 100 mcg active agent per hour to skin. Any amount of active is possible, for example the transdermal dosage form may contain anywhere from 0.1 to 500 mg of active agent. In one embodiment, the transdermal dosage form comprises fentanyl base or alkaloid in an amount of about 1 to about 10 mg.

In one embodiment of this disclosure, the antagonist salt and active agent are present in a single layer between the barrier and the skin-contacting surface. The layer may comprise the antagonist salt and the active agent dispersed, mixed and/or dissolved to some degree homogenously throughout a polymeric material. In another embodiment, the layer may comprise the antagonist salt and active agent where they are individually dispersed, mixed and/or dissolved prior to being set in alternating strips of active agent and antagonist salt. In another embodiment, the active agent and the first antagonist are separated by one or more spacers. In another embodiment, the active agent and the first antagonist are in a ratio of about 1:2 or 1:1.81. In another embodiment, the fentanyl base and the Naltrexone salt are in a ratio of about 1:2 or 1:1.81. In another embodiment, the fentanyl base and the Naltrexone salt are in a ratio of about 1:2 or 1:1.81. In another embodiment, the single layer comprises about 8% ionic naltrexone such as naltrexone HCl. In another embodiment, the single layer comprises ionic naltrexone such as naltrexone HCl in crystalline form. Additional excipients may also be present such as solubilizers like povidone or adhesives such as silicone adhesives.

In a more specific embodiment, the disclosure relates to a transdermal system for administering an active agent through the skin, the system having a reduced potential for abuse, comprising:

(a) a first antagonist component comprising a first antagonist salt and an active agent in base form, wherein the active agent may be for example amorphous or crystalline fentanyl or an analog thereof and the analog is selected from the group consisting of alfentanil, lofentanil, remifentanil, sufentanil and trefentanil;
(b) a second antagonist component comprising a second antagonist in base form, optionally in amorphous base form, the antagonist being releasable from system upon being ingested or substantially immersed in a solvent, and further wherein the antagonist is selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof; and
(c) a barrier layer, said barrier layer separating said first and second antagonist components, said barrier layer optionally being substantially impermeable to said active agents and/or excipients, wherein:
the release of the antagonist from the system when used transdermally such that levels are sufficiently low that the active agent's biological effect is maintained; and
the system provides release of the antagonist at a rate sufficient to provide an abuse limiting release rate ratio of the antagonist to the active agent when the dosage form is subject to abuse, e.g., upon transmucosal applications or substantial immersion of the system in the solvent.

In another embodiment, the disclosure relates to a transdermal system for administering an active agent through the skin, wherein the active agent such as fentanyl is formulated in amorphous form while the first antagonist salt such as Naltrexone HCl is in crystalline form and the second antagonist such as naltrexone base is formulated in amorphous form.

When an opioid is used as the active agent, release of the antagonist from one or both of the antagonist sources can inhibit the euphoric effect of the opioid. In some embodiments, the transdermal dosage form will inhibit the euphoric effect of an opioid if the device is used other than transdermally whether before or after the device is used by an animal or human for treating or preventing pain.

Release of the antagonists from the system, when used transdermally, is controlled so that antagonist levels are sufficiently low while maintaining the active agent's effect. In some embodiments, the active agent's effects are maintained for more than about two days. In other embodiments, the active agent's effects are maintained for more than about three days.

For example, if an abuser tries to extract an opioid from the transdermal dosage form by placing it in a solvent, including saliva, then an amount of an antagonist would also be extracted, providing a mixture of the opioid and the antagonist. The antagonist free base generally exhibits greater solubility, and in one embodiment bioavailability, in non-aqueous solvents than in aqueous solvents, while an antagonist salt generally exhibits greater solubility and, in one embodiment, bioavailability in aqueous solvents than in non-aqueous solvents. Thus, depending on the solvent of choice, if an abuser attempts to extract an opioid from the transdermal dosage form, whether aqueous or non-aqueous solvent, at least one form of the antagonist will be released along with the opioid. If a mixture of an opioid and antagonist is administered via a route other than the intended transdermal route, such a transmucosally, at least one form of the antagonist would exert its antagonistic effect to inhibit the euphoric effect of the opioid.

Referring now to FIG. 1, in one embodiment, the present disclosure comprises a transdermal dosage form 100 comprising:
a first antagonist component 120, optionally comprising a polymeric material and optionally in the form of a continuous, planar component in the form of a slab;
an second antagonist component 140 comprising an antagonist in free base form; and
optionally a barrier 130.

The first antagonist component has a proximal surface 115, which may be a skin-contacting surface and is optionally covered with a release liner 110, and a distal surface 125 which is opposed to the proximal surface 115. The barrier 130 is disposed between the distal surface 125 of the first antagonist component 120 and the second antagonist component 140. A backing 150 is disposed adjacent to the second antagonist component 140 at a location which provides an outer surface 155 of the dosage form 100. In some embodiments, a permeable backing layer 150 is adjacent to the second antagonist component 140. In other embodiments, a structured release liner 110 is located proximal to the first antagonist component 120 and functions to protect the surface of the skin-contacting first antagonist component 120 prior to use of the dosage form.

Figure 4:
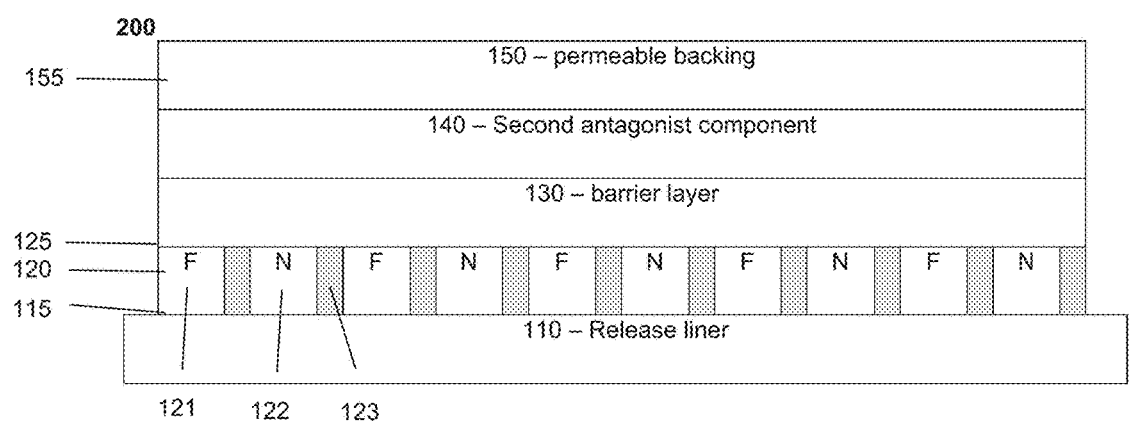
FIG. 4 is a schematic cross-section of a prototype of Example 2.

In another embodiment, shown in FIG. 4, the present disclosure comprises a transdermal dosage form 200 comprising:
a first antagonist component 120, comprising alternating strips of an active agent 121 and an antagonist in base form 122, optionally wherein the active agent and first antagonist is discontinuous having an alternating spacers 123 made up of air or voided spaces or inactive material between the active agent and antagonist strip;
a second antagonist component 140 comprising an adverse agent; and
a barrier 130.

The first antagonist component 120 has a proximal surface 115, which may be a skin-contacting surface and is optionally covered with a release liner 110, and a distal surface 125 which is opposed to the proximal surface 115. The barrier 130 is disposed between the distal surface 125 of the first antagonist component 120 and the second antagonist component 140. In some embodiments, a structured release liner 110 is located proximal to the first antagonist component 120 and functions to protect the structured surface of the skin-contacting first antagonist component 120 prior to use of the dosage form.

In one embodiment of transdermal dosage form 200, the width of the strips of active agent component 121 is greater than about 0.1 cm. In another embodiment, the width of said 121 is greater than about 0.2 cm. In another embodiment, the width of said 121 is greater than about 0.4 cm. In another embodiment, the width of said 121 is less than about 2.0 cm. In another embodiment, the width of the strips is less than 1.0 cm. In another embodiment, the width of said 121 is less than 0.6 cm. Although a specific configuration is described above, it should be understood that the alternating strips may be of any shape such as but not limited to squares, diamonds, ovals, triangles, pentagons, or hexagons.

The following relates to both FIGS. 1 and 4 above and the disclosure in general.

In one embodiment, the active agent is an opioid and the antagonist is an opioid antagonist. Opioid antagonists useful in the present disclosure include, but are not limited to, naloxone, naltrexone, nalmefene, nalbuphine, nalorphine, cyclazacine, cyclozocine, levallorphan, pharmaceutically acceptable salts thereof, and mixtures thereof. In certain embodiments, the opioid antagonist is nalmefene, naloxone, naltrexone, or a pharmaceutically acceptable salt thereof. In another embodiment, the opioid antagonist is a naltrexone. In some embodiments of this disclosure, the antagonist free base is naltrexone in amorphous form.

Useful opioid antagonist salts include salts formed from an acid and the basic nitrogen group of an opioid antagonist. Examples of opioid antagonist salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other opioid antagonist salts include salts prepared from an antagonist having an acidic functional group, such as a carboxylic acid or sulfonic acid functional group, and a pharmaceutically acceptable inorganic or organic base. In some embodiments, the antagonist salt is naltrexone hydrochloride.

The active agent or agonist will be present in an amount such that the composition delivers a therapeutically effective amount for the condition being treated. This amount will vary according to the type of active agent used, the condition to be treated, the amount of time the composition is allowed to remain in contact with the skin of the subject, and other factors known to those of skill in the art. For example, information on dosing and the amount of opioid agonist active agent present in a transdermal dosage form is set forth in U.S. Published Patent Application No. 2002/0119187 and U.S. Published Patent Application No. 2003/0026829 each of which are incorporated by reference herein in their entirety for all purposes. In one embodiment, the amount of active agent present in the transdermal drug delivery composition of the disclosure is greater than about 0.01 wt-%, based on the total weight of the composition of the active agent component. In another embodiment, the amount of active agent present in the transdermal drug delivery composition of the disclosure is greater than about 1.0 wt-%, based on the total weight of the composition of the active agent component. In another embodiment, the amount of active agent present in the transdermal drug delivery composition of the disclosure is less than about 40 wt-%, based on the total weight of the composition of the active agent component. In another embodiment, the amount of active agent present in the transdermal drug delivery composition of the disclosure is less than about 20.0 wt-%, based on the total weight 16 of the composition of the active agent component.

The analgesically effective amount of an opioid present in the transdermal dosage form typically ranges from about 0.01 to about 50 mg/cm$^2$ in one embodiment, from about 0.05 to about 15 mg/cm$^2$ in another embodiment, and from about 0.05 to about 5.0 mg/cm$^2$ in another embodiment. It is well within the purview of one skilled in the art to readily determine the analgesically effective amount of an opioid needed for a particular indication.

In one embodiment, the antagonist free base and an antagonist salt are present in an amount sufficient to inhibit at least one biological effect of an active agent. In a further embodiment, the antagonist free base and an antagonist salt are provided in a total amount sufficient to inhibit the euphoric effect of an opioid when the transdermal dosage form is subjected to abuse or misuse.

Depending on the type of abuse, the adverse agent present in transdermal patch 100 or 200, the adverse agent is capable of containing a sufficient amount of adverse agent to blunt or block at least one biological effect of the active agent or to cause at least one unpleasant side effect in a patient or animal when the patch is subjected to abuse or misuse. This amount can vary according to the amount and type of active agent in the dosage form. The amount may be included in each adverse agent component individually or combined in component 140 and component 120 depending on desired effect and form of the formulation.

The antagonist components comprise an adverse agent in any form or composition or reservoir which allows the antagonist to be at least partially extracted in the presence of a solvent, including but not limited to, water, ethanol or ether, or mixtures thereof. In certain embodiments, the antagonist can be dispersed, mixed and/or dissolved in a polymeric material, including but not limited to, the polymeric materials which are suitable for incorporation into the active agent component.

In one embodiment of the present disclosure, the dosage form is provided such that the antagonist is not absorbed to any biologically significant degree into a blood stream when administered transdermally. In other embodiments, the dosage form is provided such that the ratio of adverse agent to active agent in the dosage form is from about 1:10 to about 10:1. In other embodiments, the dosage form is provided such that the ratio of adverse agent to active agent in the dosage form is more than 3:1. In another embodiment of the present disclosure, there is provided a transdermal dosage form having reduced potential for abuse comprising an antagonist to agonist weight ratio of about 4:1. The transdermal dosage form of the present disclosure would also have stability, adhesive properties as required by pharmaceutical regulatory approval.

In another embodiment, the ratio of adverse agent to active agent released from the dosage form when the dosage form is tampered with, e.g., chewed, extracted, mechanically violated, is at least 1:5, 1:4, 1:3, 1:2, or 1:1. In another embodiment, the ratio of adverse agent to active agent released from the dosage form when the dosage form is tampered with, e.g., chewed, extracted, mechanically violated, is at least 1:1 at numerous time points between 5 min. to 4 hours.

In some embodiments, the proximal surface 115 has a release liner 110 which is removed to reveal a skin-contacting surface which should be sufficiently conformable when placed on a skin surface so as to make intimate contact with at least a portion of the skin surface. In one embodiment, substantially all of the polymeric material of the proximal surface of the first antagonist component 120 will make intimate contact with the skin surface of a patient. Suitable release liners include conventional release liners comprising a known sheet material such as a polyester web, a polyethylene web, a polypropylene web, or a polyethylene-coated paper coated with a suitable fluoropolymer or silicone based coating. The release liner that has been coated with the first antagonist component 120 can be dried and laminated onto a barrier component 120 using conventional methods.

In one embodiment, the first antagonist component 120 comprises a polymeric material, an active agent and an antagonist salt. Suitable polymeric materials or matrices for use in the first antagonist or adverse agent component include, but are not limited to, acrylates, natural rubbers, polyisobutylenes, polyisoprenes, styrenic block copolymers, polyvinylethers, silicone polymers, polyurethanes, and polyurethane-ureas. In one embodiment, the active agent or adverse agent is preferably dispersed substantially homogeneously throughout a polymeric material. In one embodiment, the active agent or adverse agent is dissolved in the polymeric material. In another embodiment, the active agent is substantially in amorphous form. In another embodiment, the adverse agent component includes a crystalline form substantially dispersed throughout the polymeric material.

In certain embodiments, the polymeric matrix is a pressure sensitive adhesive. Suitable pressure-sensitive adhesives include those suitable for use as the polymeric material of the active agent component. Additionally, pressure-sensitive adhesives that are not suitable for direct skin contact can be suitable for use as the polymeric material of the active agent or adverse agent. In some embodiments, pressure-sensitive adhesives for use in the dosage forms of the disclosure include acrylates, polyisobutylenes, silicone polymers, and mixtures thereof. Examples of useful polyisobutylene pressure-sensitive adhesives are described in U.S. Pat. No. 5,985,317, the disclosure of which is incorporated herein by reference in its entirety for all purposes. Examples of useful acrylate and silicone polymer pressure-sensitive adhesives, and mixtures thereof, are described in U.S. Pat. No. 5,474,783, the disclosure of which is incorporated herein by reference in its entirety for all purposes.

Acrylate polymers and copolymers may include pressure-sensitive adhesives. Examples of suitable monomers for use in acrylate copolymers include alkyl acrylates, such as isooctyl, 2-ethylhexyl, n-butyl, ethyl, methyl, and dimethylhexyl, and alkyl methacrylates, such as lauryl, isodecyl, and tridecyl. Monomers containing functional groups, such as carboxylic acid, hydroxy, amide, and amino may also be incorporated into an acrylate copolymer. Examples of suitable monomers containing functional groups include acrylic acid, hydroxyalkyl acrylates containing 2 to 4 carbon atoms in the hydroxyalkyl group, acrylamide, N-vinyl-2-pyrrolidone, vinyl acetate, and alkoxyethyl acrylates.

Acrylate copolymers may optionally further comprise a substantially linear macromonomer copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference in its entirety for all purposes.

Other polymer materials of the first antagonist component may include but are not limited to polyethylene; polypropylene; ethylene/propylene copolymers; ethylene/ethylacrylate copolymers; ethylene/vinyl acetate copolymers; silicone elastomers, especially the medical-grade polydimethylsiloxanes; neoprene rubber; polyisobutylene; chlorinated polyethylene; polyvinyl chloride; vinyl chloride-vinyl acetate copolymer; polymethacrylate polymer (hydrogel); polyvinylidene chloride; poly(ethylene terephthalate); butyl rubber; epichlorohydrin rubber; ethylene-vinyl alcohol copolymer; ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methylcellulose, and cellulose esters; polycarbonates; polytetrafluoroethylene; and combinations thereof. In one embodiment, the polymer matrix has a glass-transition temperature below room temperature. The polymer can, but need not necessarily, have a degree of crystallinity at room temperature. Cross-linking monomeric units or sites can be incorporated into the polymers. For example, cross-linking monomers can be incorporated into polyacrylate polymers. The cross-linking monomers provide sites for cross-linking the polymer matrix after microdispersing the active agent into the polymer. Known cross-linking monomers for polyacrylate polymers include, but are not limited to, polymethacrylic esters of polyols such as butylene diacrylate and dimethacrylate, trimethylol propane trimethacrylate, and the like. Other monomers that provide cross-linking sites include allyl acrylate, allyl methacrylate, diallyl maleate, and the like. In one embodiment the polymer matrix does not allow any, or any detectable amount, of an active agent or adverse agent to diffuse out of it, particularly in those instances in which the active agent or adverse agent can penetrate a patient's skin.

The first antagonist component can also comprise a porous medium, such as a woven fabric, porous or microporous film, or other open, mesh-like material, wherein at least a portion of the pores contain active agent or adverse agent. The active agent or adverse agent can be present within the pores in any form, including but not limited to a liquid, a gel or a solid, such as a solid crystalline or powdered material. For example, the active agent or adverse agent can be mixed with a carrier, such as a viscous liquid, semi-solid or gel material. Examples of suitable materials for incorporation into the active agent or adverse agent component include, but are not limited to, microporous films formed by extruding polyethylene or polypropylene with mineral oil as described in U.S. Pat. No. 4,539,256, the disclosure of which is incorporated herein by reference in its entirety.

Each of the layers comprising active agent or antagonist may comprise a number of additional components. Additional components of the active agent or first antagonist component can include skin penetration enhancers, drug solubilizers, plasticizers, anti-oxidants, colorants, bittering agent and the like.

The first antagonist component will typically comprise a skin penetration enhancer. Examples of excipients useful as skin penetration enhancers or solubilizers in transdermal drug delivery systems include $C_8$-$C_{24}$ fatty acids such as isostearic acid, octanoic acid, and oleic acid; $C_8$-$C_{24}$ fatty alcohols such as oleyl alcohol and lauryl alcohol; lower alkyl esters of $C_8$-$C_{24}$ fatty acids such as ethyl oleate, isopropyl myristate, butyl stearate, and methyl laurate; monoglycerides of $C_8$-$C_{24}$ fatty acids such as ethyl oleate, isopropyl myristate, butyl stearate, and methyl laurate; monoglycerides of $C_8$-$C_{24}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); polyethylene glycol; propylene glycol; N,N-dimethyldodecylamine-N-oxide; terpenes, such as d-limonene, menthol, and terpineol.

The skin penetration enhancers, drug solubilizers, plasticizers, and other additives can be dispersed or mixed, optionally substantially uniformly, or optionally dissolved in the composition. Where the additive is a penetration enhancer, it is present in an amount that enhances active agent permeation through the skin compared to a like composition not containing the penetration enhancer(s) when this phenomenon is measured using a standard skin penetration model, such as set forth in U.S. Pat. No. 5,585,111, the disclosure of which is herein incorporated by reference in its entirety. In one embodiment, the total amount of penetration enhancer and solubilizer is less than about 40% by weight based on the total weight of the composition.

In another embodiment, the total amount of penetration enhancer and solubilizer is less than about 30% based on the total weight of the composition.

A solubility enhancer may also be included. In one embodiment, the solubility enhancer is in an amount more than 2%. In another embodiment, it is in an amount of between 2.5 to 3.5%. In one embodiment, polyvinylpyrrolidone (PVP) is used.

In the first antagonist component, the active agent and antagonist, whether formulated together or separately in strips are optionally dispersed homogeneously throughout the polymeric material, or optionally dissolved within the polymeric material. The proximal or skin-contacting surface 115 should be sufficiently conformable when placed on a skin surface so as to make intimate contact with at least a portion of the skin surface. In one embodiment, substantially all of the polymeric material at the proximal surface 115 will make intimate contact with the skin surface.

In one embodiment, the first antagonist component and the antagonist each have a thickness of no less than about 10 µm. In another embodiment, the first antagonist agent component has a thickness of no less than about 20 µm. In another embodiment, the first antagonist component has a thickness of no less than about 50 µm. In another embodiment, the first antagonist component has a thickness of no greater than about 250 µm. In another embodiment, the first antagonist component has a thickness of no greater than about 200 µm. In another embodiment, the first antagonist component has a thickness of no greater than about 150 µm.

The barrier 130, as shown in FIGS. 1 and 4, is a substantially continuous component adjacent to the distal surface of the first antagonist component 120 on one side and the second antagonist component 140 on the other side. The barrier layer is impermeable to the antagonist and the active agent; and comprises a material which is insoluble in water, alcohol and organic solvents. The barrier layer comprises a polymer such as polyolefin laminates (Dow Chemical, Midland, Mich.), acrylonitrile copolymer films (BAREX, BP Chemicals, Koln, Germany), polyethylnapthalene (PEN), polyethylene terephthalate (PET), polyimide, polyurethane, polyethylene, metallized films and glass coated films where these films can include ethylene copolymers such as ethylene-vinyl acetate copolymer (EVA), and combinations thereof. In some embodiments, the barrier layer comprises polyester such as PET laminated to a polymer such as polyurethane, polyethylene, and ethylene copolymers. In other embodiments, the barrier layer comprises polyester such as PET laminated to ethylene copolymers such as ethylene-vinyl acetate copolymer (EVA). The barrier layer as a multilaminate layer has a thickness of about 0.075 mm (0.3 mil) to about 0.125 mm (5 mil); optionally 0.025 mm (1 mil) to about 0.1 mm (4 mil); optionally 0.0625 mm (1.5 mil) to about 0.0875 mm (3.5 mil); and optionally 0.025 mm (1 mil) to about 0.05 mm (2 mil). The polyethylene or EVA laminated layer of the PET-PE laminates improves the adhesion of the antagonist component to the backing, and serves to prevent the facile removal of the antagonist base layer from the system by the potential abuser.

In some embodiments, the backing is laminated to the surface of the antagonist base component, optionally using heat, pressure and/or an additional tie component to ensure adequate contact between the reservoir component and backing. In some embodiments, the backing is non-sticking and hydrophobic.

Any device known to those skilled in the art for transdermally delivering a therapeutic agent, particularly an opioid, to an animal can be used for the transdermal dosage form of the disclosure. For example, the transdermal dosage form can be a reservoir-type transdermal dosage form, a polymer-matrix type transdermal dosage form, or a drug-in-adhesive type transdermal dosage form. The transdermal dosage form is designed so that when contacted with the animal's skin, an analgesically effective amount of the active therapeutic agent, such as an opioid, is transdermally administered to the animal while the antagonist either remains in the transdermal dosage form and is not administered to the animal or is administered to the animal in an amount insufficient to inhibit the analgesic effect of the active agent.

The transdermal dosage forms of the disclosure can be made in the form of an article such as a tape, a patch, a sheet, a dressing or any other form known to those skilled in the art. Generally, the dosage form will be in the form of a patch of a size suitable to deliver a preselected amount of active agent through the skin.

In one embodiment, the dosage form will have a surface area greater than 5 $cm^2$. In another embodiment, the dosage form will have a surface area of greater than 10 $cm^2$. In another embodiment, the dosage form will have a surface area of less than 100 $cm^2$. In another embodiment, the dosage form will have a surface area of less than 40 $cm^2$.

Dosage forms of the present disclosure are typically packaged individually in a foil-lined pouch for storage. Dosage forms of the present disclosure may alternatively be provided in a rolled or stacked form suitable for use with a dispensing apparatus. An optional tie component, heat, and/or pressure may be used to connect the skin-contacting component with the barrier component. In addition, the skin-contacting component compositions may be directly coated onto the barrier component and subsequently dried and laminated to a release liner.

One skilled in the art will appreciate that it may be preferred to vary the order of lamination steps depending on the types and thickness of the components comprising the dosage form.

According to the methods of the disclosure, in one embodiment the transdermal dosage form is contacted with the skin of the patient and an opioid is released by the transdermal dosage form and becomes absorbed through the skin. Once absorbed into the patient, an opioid is provided in an analgesically effective amount. The transdermal dosage form can provide sustained and continuous delivery of an analgesically effective amount of an opioid. In another embodiment, on administration over the skin, the transdermal dosage form exhibits a steady state drug flux of about 1 to about 10 $\mu g/cm^2/hr$. In one embodiment, the transdermal dosage form exhibits a steady state drug flux of about 1 to about 8 $\mu g/cm^2/hr$. In one embodiment, the transdermal dosage form exhibits a steady state drug flux of about 1 to about 5 $\mu g/cm^2/hr$. In one embodiment, the transdermal dosage form exhibits a steady state drug flux of about 2 to about 3 $\mu g/cm^2/hr$.

In one embodiment, the transdermal dosage form exhibits a nominal flux (i.e., the average amount of drug delivered to the systemic circulation per hour across average skin) of about 12.5 mcg/hr. In one embodiment, the transdermal dosage form exhibits a nominal flux of about 50 mcg/hr. In one embodiment, the transdermal dosage form exhibits a nominal flux of about 75 mcg/hr. In one embodiment, the transdermal dosage form exhibits a nominal flux of about 100 mcg/hr.

In one embodiment of the present disclosure, the method of treating pain with any one of the dosage forms described herein, wherein said dosage form can provide a ratio of adverse agent to active agent released, or alternatively absorbed into a blood stream, from about 1:10 to about 10:1 when the dosage form is used in an inappropriate manner. For example, it may be attempted to extract the active agent from the dosage form with a solvent, such as a quid or gas. In certain embodiments, the dosage form, when tampered with in such a manner, will release both adverse and active agent. In certain embodiments, the ratio of adverse agent to active agent released when tampered with is about is 1:5, 1:4, 1:3, 1:2, or 1:1. In other embodiments, the method of treating pain comprises applying a dosage form as described herein, wherein said dosage from comprises a ratio of adverse agent to active agent from about 1:10 to about 10:1. In other embodiments, the ratio of adverse agent to active agent is about is 1:5, 1:4, 1:3, 1:2, or 1:1.

The present disclosure is also directed to a kit comprising at least one dosage form of the disclosure. In one embodiment, the dosage form is present in a container, e.g., a box. In another embodiment, the kit further comprises a set of instructions directing the use of the dosage form to treat a patient, e.g., for pain. In one embodiment, the instructions may be a printed label affixed to or printed on the container. In another embodiment, the instructions may comprise a printed sheet inserted into the container or into the packaging which contains the container. The instructions may also state that the dosage form and/or its usage are designed to reduce abuse, misuse or diversion of the dosage form.

EXAMPLES

Example 1

Figure 3:
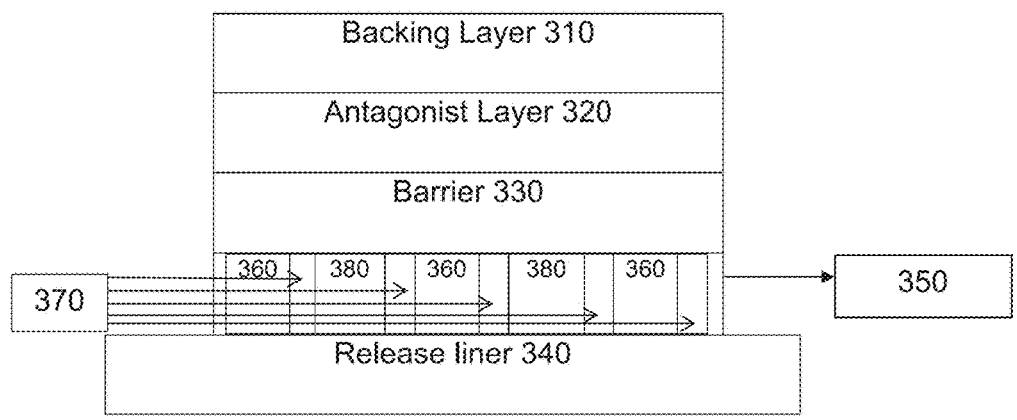
FIG. 3 is a schematic cross-section of a prototype of Example 1.

The transdermal dosage form Patch A1 as depicted in FIGS. 3 and 4 were prepared according to the manufacturing process steps described below. The quantitative composition of component of the Patch A1 is provided below in Tables.

Patch A1 was manufactured according to the amounts below in Table 1 and according to the following process steps:

1. Manufacturing skin contact layer fentanyl wet blend and then coat to make laminate containing fentanyl base, die-cut to 10 mm strip.
2. Manufacturing skin contact layer naltrexone hydrochloride wet blend and then coat to make laminate containing naltrexone hydrochloride, die cut to 10 mm strip.
3. Manufacturing non-skin contact layer wet blend and then laminate containing naltrexone base.
4. Die-cut non skin contact layer to appropriate sized patches.
5. Apply one or more fentanyl adhesive strips to the barrier film of a non-skin contact layer patch. Apply one of more naltrexone hydrochloride adhesive strips to the barrier film of the non-skin contact layer patch with about 1 mm gap between a fentanyl strip and a naltrexone HCl strip.
6. Pouch to give finished product.

TABLE 1

| MATERIAL | % | mg 100 mcg/h | |
|---|---|---|---|
| One side silicone coated polyester fabric KOB051 | | | |
| Naltrexone base | 16.0000 | 87.36 | Naltrexone base is dispersed as amorphous form in the PVP/adhesive matrix |
| Povidone K90 | 16.0000 | 87.36 | |
| Bio-PSA 7-4302 | 34.0000 | 185.64 | |
| Duro-Tak 387-2510 | 34.0000 | 185.64 | |
| Scotchpak 9735 barrier film Three 10 mm wide strips and three 10 mm side naltrexone base strips, 1 mm spacer between each fentanyl strip and each naltrexone strip | | | |
| Fentanyl strip: | | | |
| Fentanyl alkaloid micronized crystals (microcrystals) | 4.0000 | 10.08 | Fentanyl base microcrystals are suspended in the adhesive matrix |
| Bio-PSA 7-4301 | 47.9998 | 120.959 | |
| Bio-PSA 7-4201 | 47.9998 | 120.959 | |
| Denatonium benzoate (bittering agent) | 0.0005 | 0.0125 | |
| Naltrexone strip: | | | |
| Naltrexone HCl (microcrystals) | 16.0000 | 40.32 | Naltrexone HCl microcrystals are suspended in the adhesive matrix |
| Bio-PSA7-4302 | 19.5000 | 52.92 | |
| Bio-PSA 7-4202 | 19.5000 | 52.92 | |
| Duro-Tak 87-4287 | 38.9995 | 105.83 | |
| Denatonium benzoate | 0.0005 | 0.0125 | |
| Scotchpak 1022 release liner | | | |

The 12.5 mcg/h, 25 mcg/h, 50 mcg/h and 75 mcg/hr strengths are patch size/area proportional to the 100 mcg/hr patch size/area. The amount of each excipient in the 12.5 mcg/h, 25 mcg/h, 50 mcg/h and 75 mcg/hr patches is 12.5%, 25%, 50%, and 75% of the amount of the same excipient in the 100 mcg/h patch.

Example 2

Figure 2:
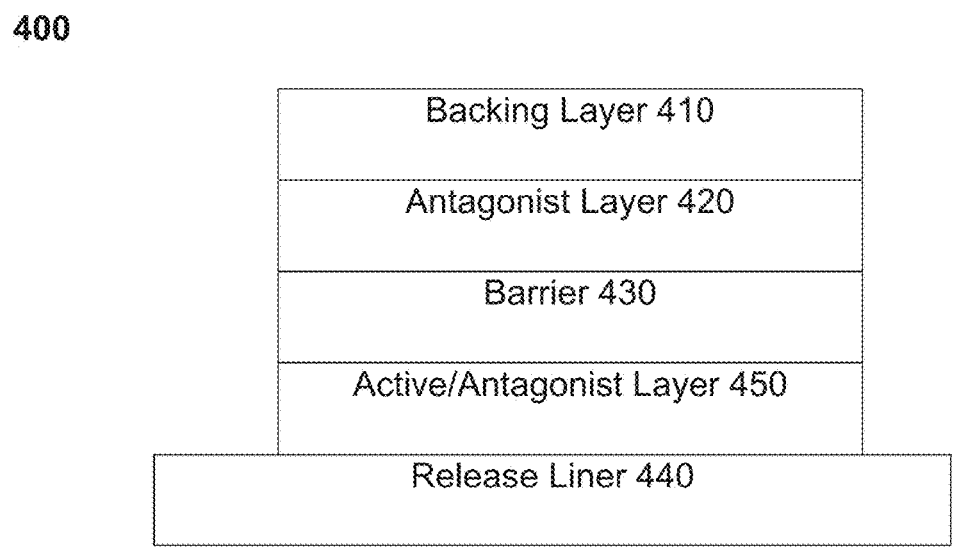
FIG. 2 is a schematic cross-section of another transdermal dosage system of the disclosure.
Figure 5:
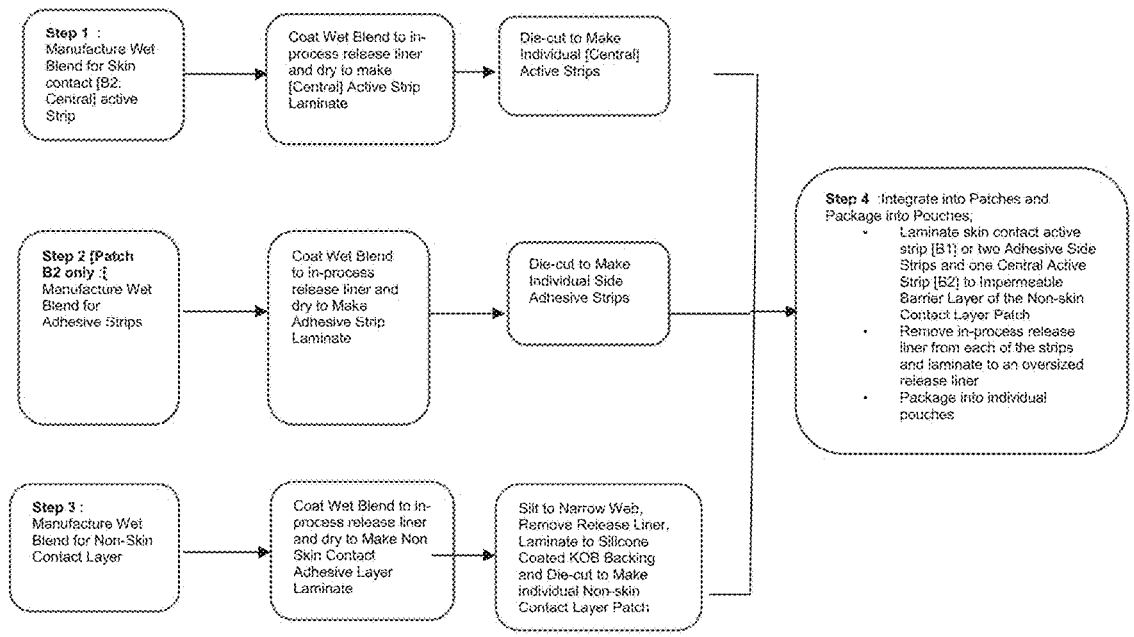
FIGS. 5-9 are manufacturing process steps for patches B1 and B2.
Figure 6:
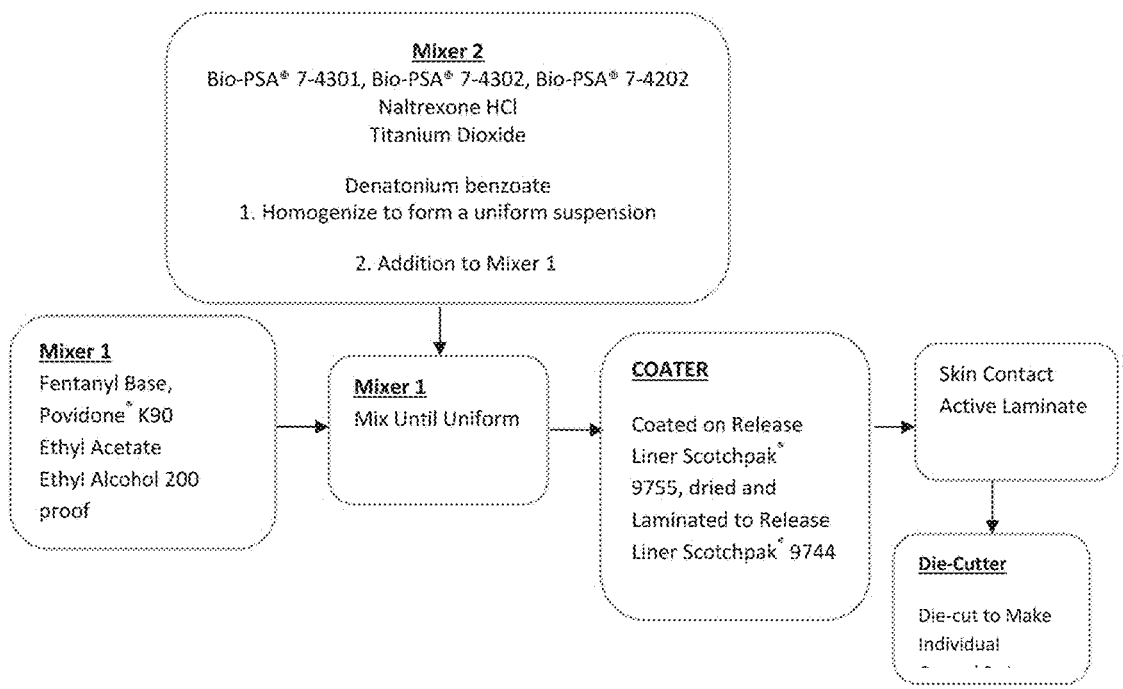
Figure 7:
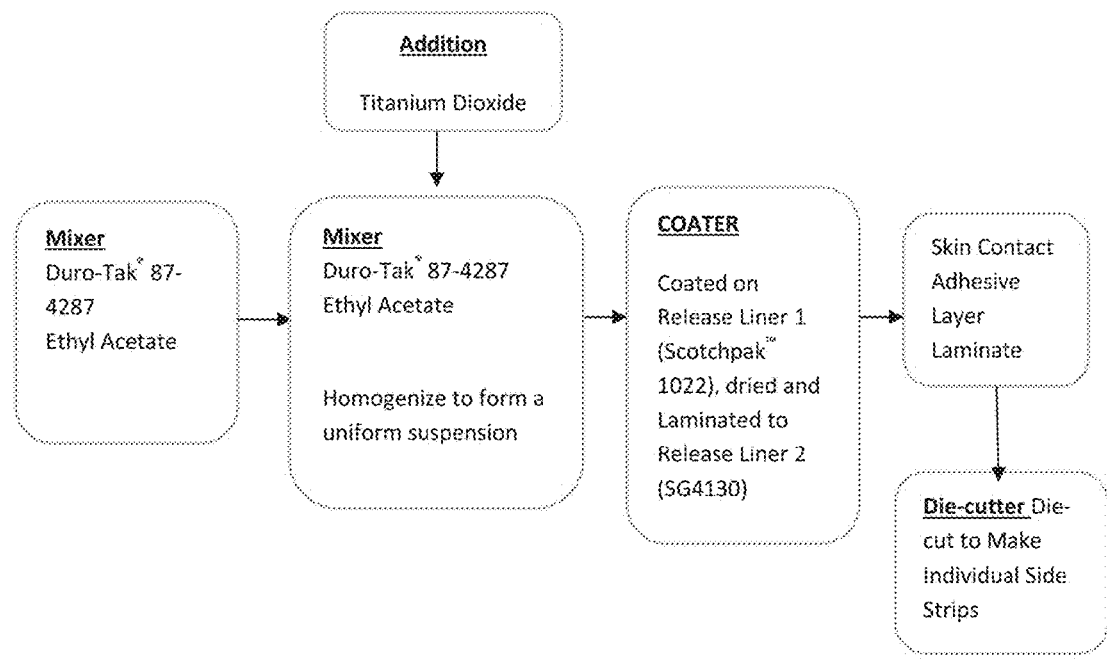
Figure 8:
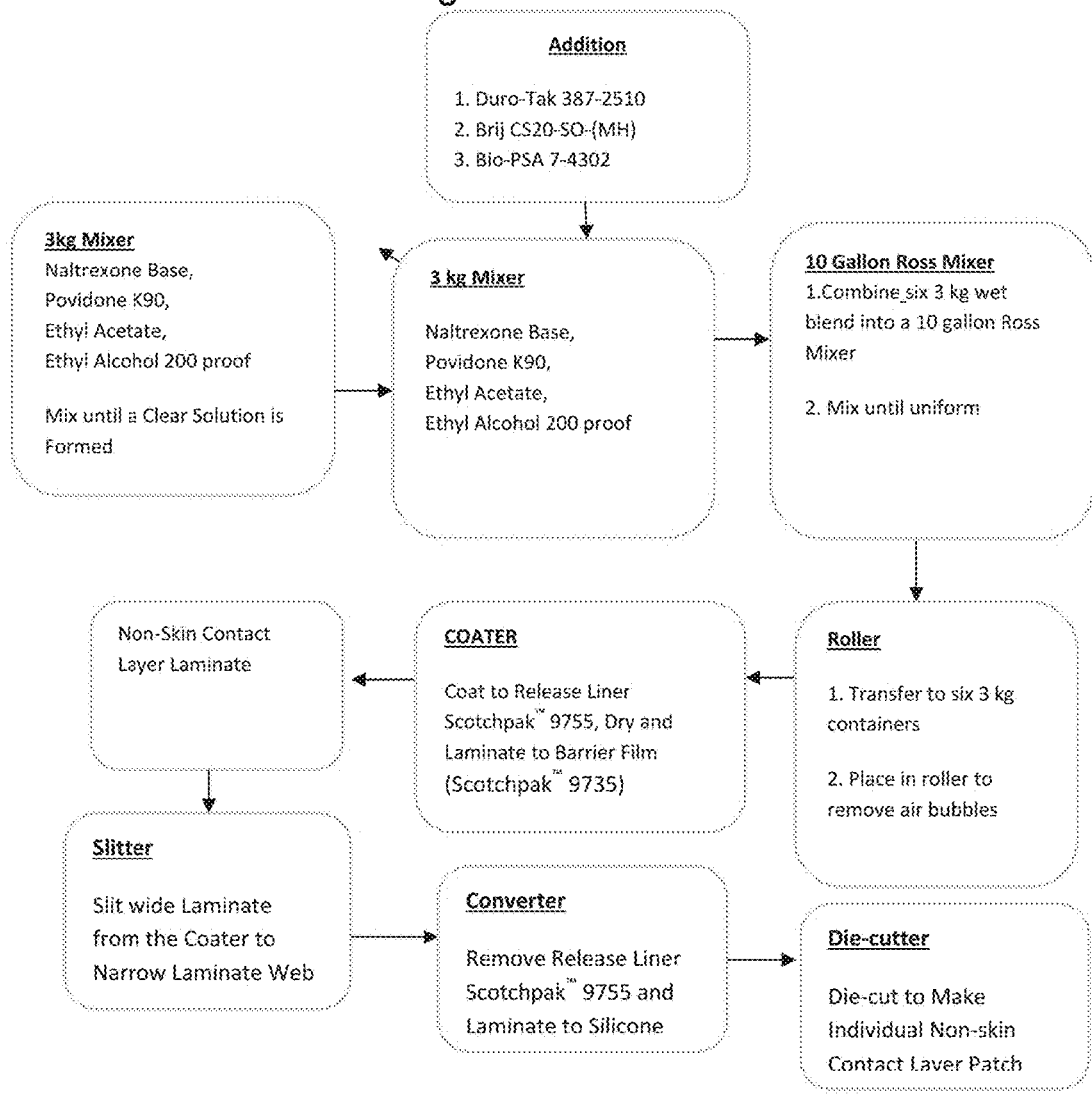
Figure 9:
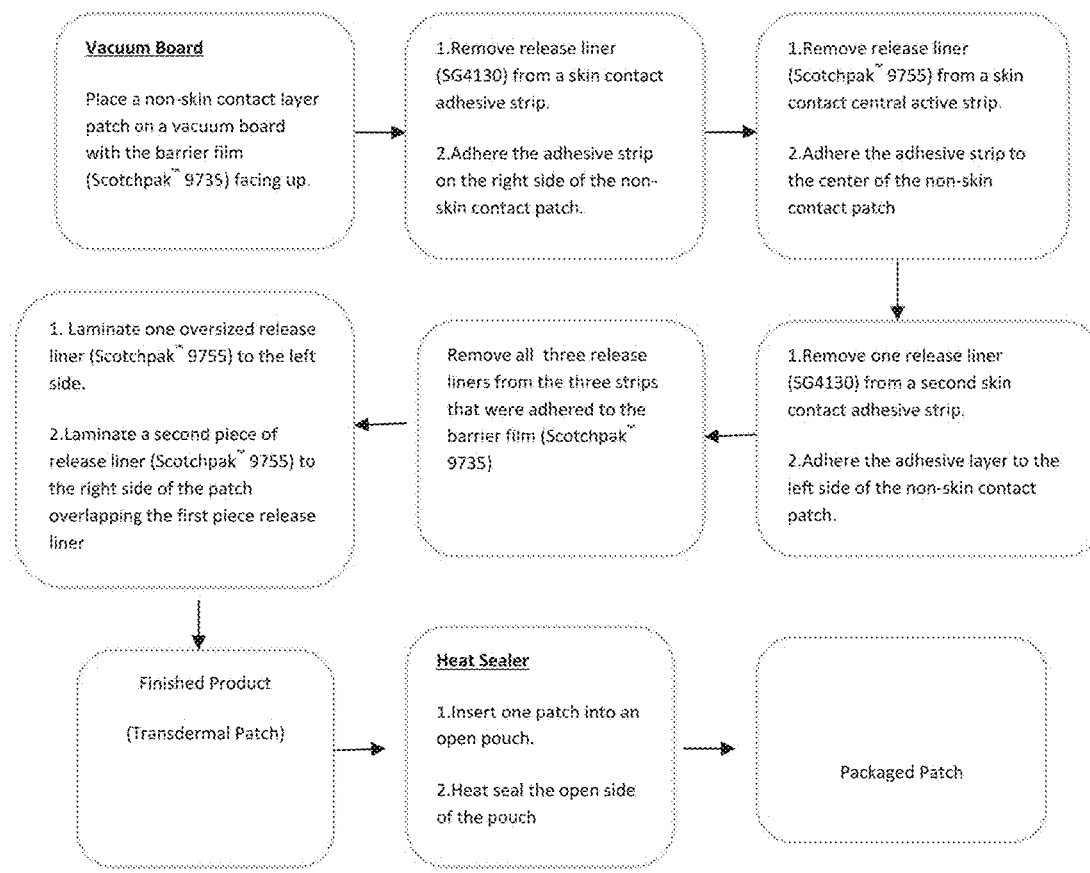

The transdermal dosage form Patch B2 as depicted in FIGS. 1 and 2 and Patch B1 as depicted in FIGS. 3 and 4 were prepared according to the manufacturing process steps described in FIGS. 5-9. FIG. 5 is a schematic of the manufacturing process steps for transdermal patch B1 and B2. FIG. 6 is a manufacturing flow diagram of the skin contact layer (central) active strip containing fentanyl base and naltrexone HCl (layer B). FIG. 7 is a schematic of the manufacturing process steps of the skin contact layer adhesive strips (Layer B) for patch B2. FIG. 8 is a manufacturing flow diagram for the non-skin contact layer (layer D) containing naltrexone (step 3). FIG. 9 is a manufacturing flow diagram for the integration of the non-skin contact layer, skin contact adhesive side strips and skin contact central active strip into the finished transdermal patch (step 4).

The quantitative composition of component of the Patch B1 and B2 is provided in Table 2. Other doses for Patch B1 can be calculated. For example, 12.5 mcg/hr is 12.5% of each mg/patch of the 100 mcg/hr fentanyl amounts.

The drug product manufacturing process consists of a four step process as described in FIG. 5. For each of the first three steps, a wet blend is coated onto an in-process release liner, dried and laminated to another release liner or a barrier film, resulting in one of the three separate intermediate adhesive laminates. During the last two steps of the manufacturing process, each of the intermediate laminates is die-cut to the appropriate size for each patch strength and assembled into the final dosage form.

The manufacturing process for Step 1 is shown in FIG. 6 and according to the following:

(i) Prepare naltrexone hydrochloride suspension in three silicone adhesives: Charge Bio-PSA® 7-4301 and Bio-PSA® 7-4202 into a Ross mixer bowl. Cool to approximately 20° C. Charge naltrexone hydrochloride and Bio-PSA® 7-4302. Homogenize to form a uniform suspension.

(ii) Prepare fentanyl and povidone solution in a mixed solvent of ethanol and ethyl acetate: Charge fentanyl base, Povidone® K90, ethyl acetate and ethanol into a Ross mixer bowl. Heat to approximately 50° C. and mix to form a clear, viscous solution.

(iii) Prepare final wet blend: Add the naltrexone hydrochloride suspension to the Ross mixer bowl containing fentanyl and povidone K90 solution. Mix at low speed for a minimum of 4 hours. This is the final wet blend.

(iv) Transfer the final wet blend to four glass containers. Place the containers in jar rollers. Rotate the jar at slow speed to remove air bubbles and to keep the naltrexone hydrochloride crystals uniformly suspended.

(v) Form Skin Contact Layer Active Laminate Strip of coat weight: Coat the final wet blend to a fluoropolymer coated polyester in-process release liner (Scotchpak™ 9755) in a continuous coater with slot-die coating knife and three-zone drying ovens at 0.3 meter/min web speed and zone temperatures (zone 1: ~65° C., zone 2: ~85° C. and zone 3: ~ 109° C.). Laminate to a fluoropolymer coated polyester in-process release liner (Scotchpak™ 9744) to form the skin contact active intermediate laminate.

(vi) Using a rotary die press, die-cut into individual [central] active strips.

The manufacturing process for Step 2 is shown in FIG. 7 and in the following:

(i) Charge Duro-Tak® 87-4287 and ethyl acetate to a Ross mixer bowl. Mix for approximately 30 min.

(ii) Charge titanium dioxide to the Ross mixer bowl. Homogenize to form a uniform suspension.

(iii) Form Skin Contact Layer Adhesive Laminate of 105 GSM coat weight: Coat the wet blend to an in-process polyester release liner with a fluoropolymer coating (Scotchpak™ 1022) in the continuous coater with slot-die coating knife and three-zone drying ovens at 0.3 meter/min web speed and zone temperature (zone 1: 65° C., zone 2: 109° C.). Laminate to an in-process silicone coated polyester release liner (SG4130). For information on the in-process release liner Scotchpak™ 1022.

(iv) Using a rotary die press, die-cut into individual adhesive strips.

The manufacturing process for Step 3 is shown in FIG. 8 and in the following:

(i) Prepare 3 kg wet blend: Charge naltrexone base, Povidone K90, ethyl acetate and ethyl alcohol to a 3 kg glass container. Heat and mix at 55° C. for about 1 hour until a clear solution is formed. Add Duro-Tak® 387-2510, Brij® CS20-SO-MH and Bio-PSA® 7-4302. Mix to form a 3 kg wet blend.

(ii) Repeat to prepare six 3 kg wet blends.

(iii) Transfer the six 3 kg wet blends to a 10 gallon Ross mixer bowl. Mix until uniform.

(iv) Transfer the wet blend from the 10 gallon mixer to six 3 kg containers. Place the 3 kg containers to roller and roll to remove air bubbles.

(v) Perform in-process testing: Description, Blend CU and Viscosity (vi) Form Non-skin Contact Layer Adhesive Laminate of 105 GSM coat weight: coat the wet blend to release liner Scotchpar 9755 in the continuous coater with slot-die coating knife and three zone drying ovens. Laminate to Barrier film Scotchpar 9735 to form the Non-skin Contact Intermediate Laminate.

(vii) In a Slitter machine, slit the wide laminate from the coater to narrower laminate.

(viii) In a Converter machine, remove the release liner (Scotchpar 9755) and laminate the drug-adhesive layer to silicone coated elastic polyester fabric KOB051 backing.

(ix) Using a rotary die press, die-cut into individual non-skin contact layer patches.

The manufacturing process for Step 4 is shown in FIG. 9 and in the following:

(i) Place a non-skin contact layer patch on a vacuum board with the barrier film (Scotchpak® 9735) facing up.

(ii) Remove one release liner (SG4130) from a skin contact adhesive strip. Adhere the adhesive layer to the right side of the non-skin contact patch.

(iii) Remove one release liner (Scotchpak® 9755) from a skin contact central active strip. Adhere the adhesive layer to the center of the non-skin contact layer.

(iv) Remove one release liner (SG4130) from a second skin contact adhesive strip. Adhere the adhesive layer to the left side of the non-skin contact layer.

(v) Remove all the 3 release liners (Scotchpak™ 1022, Scotchpak™ 9744 and Scotchpak 1022) from the three strips already adhered on the barrier film (Scotchpak™ 9735). Laminate one oversized release liner (Scotchpak™ 9755) to the left side. Laminate a second piece of release liner (Scotchpak™ 9755) to the right side of the patch overlapping the first piece of the same release liner. This forms the finished product (transdermal patch).

(vi) Insert one patch into an open pouch. Heat-seal the open side of the pouch.

TABLE 2

Quantitative Composition of Patch B1 and B2

Layer E: Semipermeable Silicone Coated Backing Layer

| Component | Patch B2 | | | | | Patch B1 |
|---|---|---|---|---|---|---|
| | 12.5 mcg/h fentanyl | 25 mcg/h fentanyl | 50 mcg/h fentanyl | 75 mcg/h fentanyl | 100 mcg/h fentanyl | 100 mcg/h fentanyl |
| Size (cm$^2$/Patch) | 8.66 | 13.92 | 23.76 | 32.51 | 39.72 | 24.00 |
| Silicone Coated Elastic Polyester Fabric KOB051 (mg/Patch) | 103.23 | 165.93 | 283.22 | 387.52 | 473.46 | 286.08 |

Layer D: Non Skin Contact Layer Formulation

| Component | % w/w | Patch B2 | | | | | Patch B1 | |
|---|---|---|---|---|---|---|---|---|
| | | 12.5 mcg/h fentanyl | 25 mcg/h fentanyl | 50 mcg/h fentanyl mg/Patch | 75 mcg/h fentanyl | 100 mcg/h fentanyl | % w/w | 100 mcg/h fentanyl mg/Patch |
| Naltrexone Base | 16.000 | 15.241 | 24.507 | 41.823 | 57.226 | 69.910 | 16.00 | 38.40 |
| Polyvinyl Pyrrolidone (Povidone ® K90) | 8.000 | 7.620 | 12.254 | 20.912 | 28.613 | 34.955 | 8.00 | 38.40 |
| Polyoxyethylene 20 Cetostearylether (Brij CS20-SO-(MH)) | 4.000 | 3.810 | 6.127 | 10.456 | 14.306 | 17.478 | 2.00 | 4.80 |
| Bio-PSA ® 7-4302 | 36.000 | 34.292 | 55.141 | 94.102 | 128.758 | 157.298 | 81.60 | 34.00 |
| Duro-Tak ® 387-2510 | 36.000 | 34.292 | 55.141 | 94.102 | 128.758 | 157.298 | 81.60 | 34.00 |
| Size (cm$^2$) | — | 8.66 | 13.92 | 23.76 | 32.51 | 39.72 | 24.00 | |
| Non Skin Contact Layer Weight Total (without including backing and barrier film), mg | 100.000 | 95.255 | 153.170 | 261.395 | 357.661 | 436.940 | 100.000 | 240.000 |

Layer C: Impermeable Barrier Layer

| Component | Patch B2 | | | | | Patch B1 |
|---|---|---|---|---|---|---|
| | 12.5 mcg/h fentanyl | 25 mcg/h fentanyl | 50 mcg/h fentanyl | 75 mcg/h fentanyl | 100 mcg/h fentanyl | 100 mcg/h fentanyl |
| Scotchpak ™ 9735 (mg/Patch) | 47.44 | 76.25 | 130.16 | 178.09 | 217.59 | 131.458 |
| Size (cm$^2$) | 8.66 | 13.92 | 23.76 | 32.51 | 39.72 | 24.00 |

Layer B: Skin Contact Active Strip Formulation

| Component | % w/w | Patch B2-Central Active Strip | | | | | Patch B1 | |
|---|---|---|---|---|---|---|---|---|
| | | 12.5 mcg/h fentanyl | 25 mcg/h fentanyl | 50 mcg/h fentanyl mg/Patch | 75 mcg/h fentanyl | 100 mcg/h fentanyl | 100 mcg/h fentanyl mg/Patch | % w/w |
| Fentanyl Alkaloid | 4.000 | 1.260 | 2.521 | 5.041 | 7.562 | 10.080 | 10.080 | 4.00 |
| Naltrexone HCl, Micronized [D90 is NMT 15 μm, D50 NMT 10 μm and D10 NMT 5 μm] | 8.000 | 2.520 | 5.041 | 10.081 | 15.123 | 20.160 | 20.160 | 8.00 |
| Polyvinyl Pyrrolidone (Povidone ® K90) | 3.000 | 0.945 | 1.891 | 3.781 | 5.671 | 7.560 | 7.56 | 3.00 |
| Titanium Dioxide | 0.300 | 0.095 | 0.189 | 0.378 | 0.567 | 0.756 | — | — |
| Bio-PSA ® 7-4301 | 55.055 | 17.343 | 34.695 | 69.379 | 104.077 | 138.739 | 160.650 | 63.750 |
| Bio-PSA ® 7-4302 | 12.705 | 4.002 | 8.007 | 16.011 | 24.018 | 32.017 | — | — |
| Bio-PSA ® 7-4202 | 16.94 | 5.336 | 10.675 | 21.347 | 32.024 | 42.689 | −53.537 | −21.245 |
| Skin Contact Layer's Active Strip Size (cm$^2$) | — | 3.13 | 6.14 | 12.13 | 18.14 | 24.14 | 24.00 | — |
| Denatonium benzoate | — | — | — | — | — | — | 0.012 | 0.0005 |
| Skin Contact Layer's Active Strip Weight Total (mg) | 100.000 | 31.502 | 63.019 | 126.018 | 189.041 | 252.000 | 252.000 | 100.00 |

TABLE 2-continued

Quantitative Composition of Patch B1 and B2

Layer B: Skin Contact Adhesive Strip Formulation

| Component (mg/Patch) | % w/w | Patch B2 | | | | |
|---|---|---|---|---|---|---|
| | | 12.5 mcg/h fentanyl | 25 mcg/h fentanyl | 50 mcg/h fentanyl | 75 mcg/h fentanyl | 100 mcg/h fentanyl |
| Titanium Dioxide | 0.300 | 0.163 | 0.230 | 0.343 | 0.424 | 0.460 |
| Duro-Tak ® 87-4287 | 99.700 | 54.150 | 76.354 | 114.040 | 140.986 | 152.857 |
| Skin Contact Layer's Adhesive Strip Size (cm$^2$) | — | 5.31 | 7.431 | 11.031 | 13.605 | 14.739 |
| Skin Contact Layer's Adhesive Strips Weight Total (without including release liner; mg) | 100.000 | 54.313 | 76.583 | 114.383 | 141.410 | 153.317 |

Layer A: Release Liner

| Component | Patch B2 | | | | | Patch B1 |
|---|---|---|---|---|---|---|
| | 12.5 mcg/h fentanyl | 25 mcg/h fentanyl | 50 mcg/h fentanyl | 75 mcg/h fentanyl | 100 mcg/h fentanyl | 100 mcg/h fentanyl |
| Scotchpak ™ 9755 (mg/Patch) | 150.56 | 218.65 | 341.33 | 448.05 | 534.55 | 401.97 |
| Size (cm$^2$) | 14.15 | 20.55 | 32.08 | 42.11 | 50.24 | 37.78 |

Total Patch

| | Patch B2 | | | | | Patch B1 |
|---|---|---|---|---|---|---|
| | 12.5 mcg/h fentanyl | 25 mcg/h fentanyl | 50 mcg/h fentanyl | 75 mcg/h fentanyl | 100 mcg/h fentanyl | 100 mcg/h fentanyl |
| Total Patch Size (cm$^2$) | 8.66 | 13.92 | 23.76 | 32.51 | 39.72 | 24.00 |
| Total Patch Weight (without including backing, barrier film and release liner) (mg/patch) | 181.070 | 292.772 | 501.796 | 688.113 | 842.258 | 492.00 |

Example 3

Solvent extraction in buffered saline was determined using the test method described for Patch A1 and B2.

Extraction Method

The test samples were transdermal patches: Patch A1 (6.25 cm$^2$) and Patch B2 (6 cm$^2$). The extraction solution was chosen from one of the following solutions at room temperature and 70° C.: water; ethanol (USP, absolute); pH6.8 Phosphate Buffer; cooking vinegar; and artificial saliva.

The patch and a 15 mL extraction solution were added into a 40 mL vial. The sealed vial was vigorously shaken with a wrist-action shaker (Burrel, Model 75, speed setting: 10). At fixed time intervals of 5, 15, and 30 minutes aliquots were removed. Each aliquot was placed into an analysis vial. If the extraction solvent was ethyl acetate or ether, then it was evaporated to dryness and methanol (HPLC grade) was added to the sample and mixed. Samples were assayed for active drug substance by reverse-phase HPLC.

TABLE 3

Solvent Extraction Test Results

| | | | Average Ratio (Wt$_{Naltrexone}$/Wt$_{Fentanyl}$) | | Average amount (mg) | | | |
|---|---|---|---|---|---|---|---|---|
| | | | | | Patch A1, 25 mcg/hr, 6.25 cm$^2$ | | Patch B2, 25 mcg/hr, 6 cm$^2$ | |
| | | | (n = 2) | | Fentanyl | Naltrexone | Fentanyl | Naltrexone |
| | T (C.) | Time (min) | Patch A1, 25 mcg/hr, 6.25 cm$^2$ | Patch B2, 25 mcg/hr, 6 cm$^2$ | Base Theoretical Value: 2.50 mg | Base Theoretical Value: 31.05 mg | Base Theoretical Value: 2.52 mg | Base Theoretical Value: 14.15 mg |
| Water | RT | 10 | 33.0 | 3.4 | 0.12 | 3.79 | 0.93 | 3.14 |
| | | 30 | 31.3 | 3.6 | 0.14 | 4.38 | 0.99 | 3.53 |
| | | 120 | 32.6 | 4.5 | 0.14 | 4.57 | 0.82 | 3.63 |

TABLE 3-continued

Solvent Extraction Test Results

| | | | Average Ratio ($Wt_{Naltrexone}/Wt_{Fentanyl}$) (n = 2) | | Average amount (mg) | | | |
|---|---|---|---|---|---|---|---|---|
| | | | | | Patch A1, 25 mcg/hr, 6.25 cm² | | Patch B2, 25 mcg/hr, 6 cm² | |
| | T (C.) | Time (min) | Patch A1, 25 mcg/hr, 6.25 cm² | Patch B2, 25 mcg/hr, 6 cm² | Fentanyl Base Theoretical Value: 2.50 mg | Naltrexone Base Theoretical Value: 31.05 mg | Fentanyl Base Theoretical Value: 2.52 mg | Naltrexone Base Theoretical Value: 14.15 mg |
| Ethanol | 70 C. | 10 | 12.2 | 4.8 | 0.55 | 6.70 | 0.87 | 4.16 |
| | | 30 | 19.6 | 6.6 | 0.50 | 9.81 | 0.90 | 5.89 |
| | | 120 | 56.0 | 13.3 | 0.23 | 12.60 | 0.59 | 7.82 |
| | RT | 10 | 12.8 | 5.9 | 2.48 | 31.73 | 2.28 | 13.38 |
| | | 30 | 12.8 | 6.0 | 2.34 | 29.88 | 2.19 | 13.13 |
| | | 120 | 12.8 | 6.1 | 1.96 | 25.08 | 1.80 | 10.98 |
| | 70 C. | 10 | 12.9 | 5.9 | 2.37 | 30.54 | 2.33 | 13.81 |
| | | 30 | 12.9 | 6.0 | 2.25 | 28.95 | 2.25 | 13.37 |
| | | 120 | 13.0 | 6.0 | 1.96 | 25.39 | 1.85 | 11.09 |
| pH 6.8 Phosphate Buffer | RT | 10 | 8.1 | 2.5 | 0.44 | 3.57 | 1.55 | 3.93 |
| | | 30 | 7.4 | 2.4 | 0.62 | 4.57 | 1.70 | 4.10 |
| | | 120 | 6.7 | 2.6 | 0.65 | 4.34 | 1.44 | 3.70 |
| | 70 C. | 10 | 8.7 | 3.7 | 1.13 | 9.77 | 1.55 | 5.73 |
| | | 30 | 17.0 | 5.3 | 0.93 | 15.86 | 1.66 | 8.71 |
| | | 120 | 32.2 | 9.1 | 0.59 | 18.87 | 1.02 | 9.25 |
| Cooking Vinegar | RT | 10 | 15.5 | 5.4 | 0.31 | 4.79 | 1.04 | 5.61 |
| | | 30 | 14.8 | 5.2 | 0.35 | 5.20 | 1.02 | 5.32 |
| | | 120 | 14.1 | 4.8 | 0.36 | 5.07 | 0.81 | 3.87 |
| | 70 C. | 10 | 7.9 | 4.6 | 0.81 | 6.42 | 1.22 | 5.55 |
| | | 30 | 6.3 | 4.9 | 1.33 | 8.39 | 1.40 | 6.87 |
| | | 120 | 5.6 | 4.8 | 1.78 | 9.90 | 1.26 | 6.03 |
| Artificial Saliva | RT | 10 | 10.8 | 2.7 | 0.31 | 3.36 | 0.85 | 2.30 |
| | | 30 | 8.5 | 2.7 | 0.53 | 4.52 | 1.09 | 2.89 |
| | | 120 | 7.4 | 2.7 | 0.66 | 4.83 | 0.93 | 2.51 |
| | 70 C. | 10 | 5.5 | 3.7 | 1.40 | 7.72 | 1.57 | 5.87 |
| | | 30 | 14.1 | 5.2 | 0.93 | 13.03 | 1.56 | 8.13 |
| | | 120 | 39.7 | 10.0 | 0.41 | 16.06 | 0.84 | 8.31 |

Example 4

Figure 10:
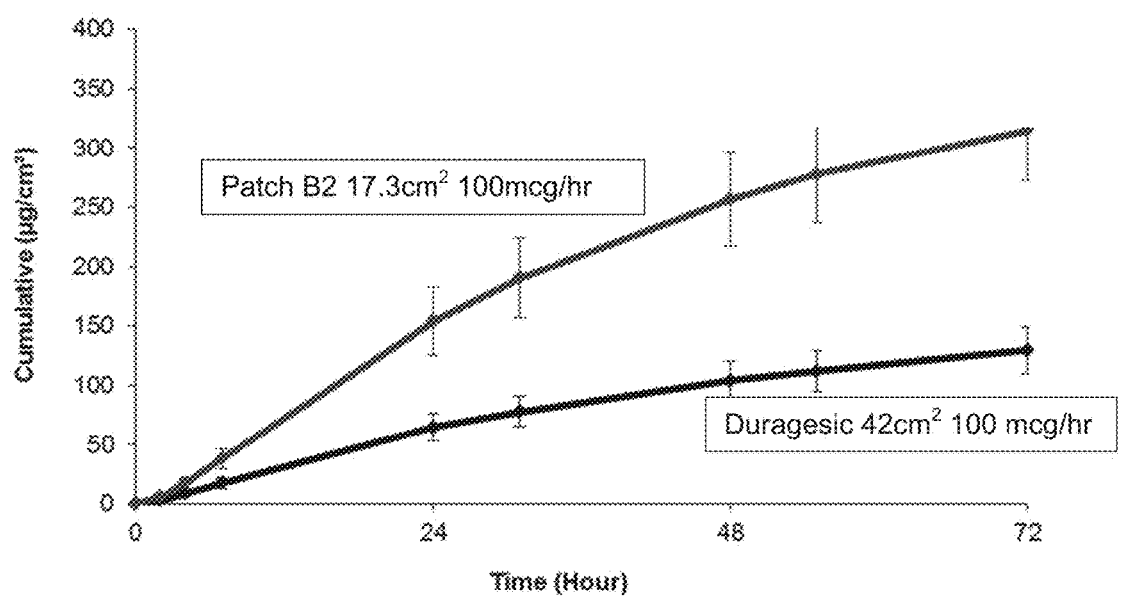
FIG. 10 is a line graph showing in vitro cumulative delivery per $cm^2$ of Patch B2 versus the Duragesic® patch.
Figure 15:
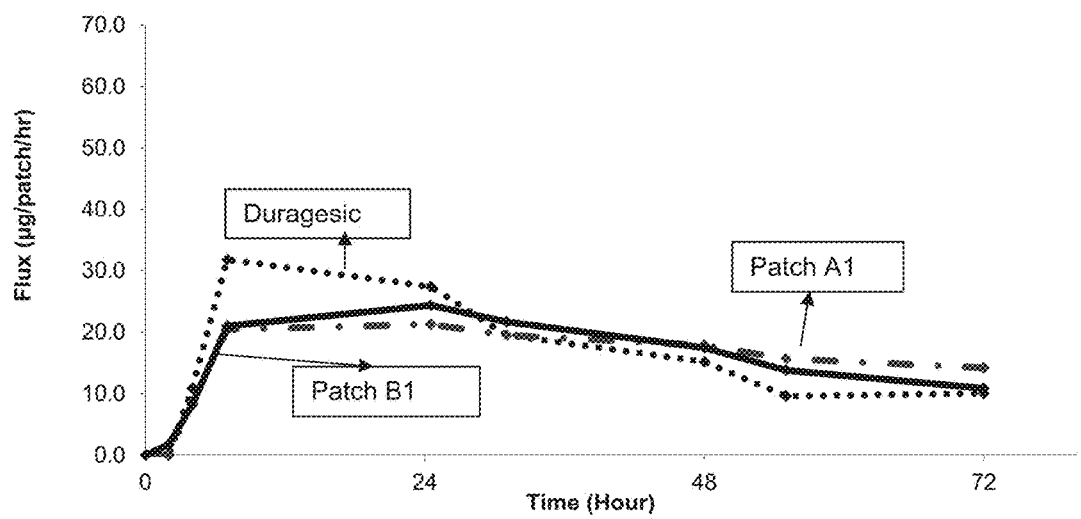
FIG. 15 is a line graph showing in vitro results for patch B1 (solid line), patch A1 (dotted line; - -♦- -), and a Duragesic® patch (dotted line; •••♦•••).

Both Patch A1 and Patch B1 were shown to be similar to the Duragesic® product as tested in a standard in vitro skin flux tests. FIG. 15 shows the in vitro results where the solid line is for patch B1, dotted line (- -◆- -) is for patch A1, and dotted line (•••◆•••) is for Duragesic®. FIG. 10 shows in vitro cumulative delivery per cm² of Patch B2 versus the Duragesic® patch.

Example 5

TABLE 4

AD fentanyl—Sum of In vitro results

| Target Product Profile | Target In Vitro Criteria | In Vitro Results | |
|---|---|---|---|
| A patch containing fentanyl and naltrexone. Fentanyl Abuse deterrence will be using a defined ratio of fentanyl to naltrexone. Once the patch is tampered with, the naltrexone will be released, making fentanyl non-useable. As long as transdermal patch | | | |
| | | Patch A1 | Patch B2 |
| Patch will be effective to deter the following routes of abuse: Transmucosal route delivery: buccal, sublingual, rectal insertion and nasal insertion, GI delivery or injection. | Transmucosal route deterrent effectiveness is measured by the amount of each naltrexone and fentanyl buccal delivery and ratio; IV route deterrent effectiveness is measured by the amount of each naltrexone and fentanyl and ratio. | | |
| Pain management efficacy | Fentanyl is bioequivalent to Duragesic ® | In vitro fentanyl skin flux is equivalent to Duragesic ® (i.e., the 72 hr cumulative delivery of the Test patch equals to that of Duragesic ® patch) | Yes | Yes |
| | No or low level of naltrexone skin delivery resulting in plasma $C_{ss}$ < 0.2 ng/ml | Naltrexone $C_{ss}$ predicted as per in vitro skin flux < 0.2 ng/ml; $C_{ss}$ = ng/ml | 0.007 | 0.030 |

TABLE 4-continued

AD fentanyl—Sum of In vitro results

Target Product Profile
Target In Vitro Criteria
A patch containing fentanyl and naltrexone. Fentanyl Abuse deterrence will be using a defined ratio of fentanyl to naltrexone. Once the patch is tampered with, the naltrexone will be released, making fentanyl non-useable. As long as transdermal patch

| | Target Product Profile | Target In Vitro Criteria | In Vitro Results | |
|---|---|---|---|---|
| Transmucosal route deterrent efficacy | Naltrexone buccal flux is high | Average in vitro naltrexone buccal flux (0.25, 1 and 1.5 hr), μg/patch | 680.65 | 1435.20 |
| | Fentanyl buccal flux is low | Average In vitro fentanyl buccal flux (0.25, 1 and 1.5 hr): μg/patch | 73.08 | 475.20 |
| | Effective naltrexone to fentanyl ratio to deter oral mucosal abuse is >1 | Ratio of naltrexone buccal flux: fentanyl buccal flux within (0.25, 1, 15 hr) is ≥1 | 9.31 | 3.02 |
| IV deterrent efficacy | Effective naltrexone to fentanyl ratio to deter IV abuse is >1 | Small volume extraction results in a high ratio of naltrexone: fentanyl (5 different solvents) | 2 or >>2 | >2 |
| Drug Loading | Naltrexone loading per 100 mcg/h patch is sufficient high to deter abuse; mg/patch | | 127.36 | 54.40 |
| | Fentanyl loading per 100 mcg/h patch ≤16.8 mg (in Duragesic ® patch) | Fentanyl loading per 100 mcg/h ad fentanyl patch ≤ 16.8 mg (in Duragesic ® patch): mg/patch | 10 | 8.8 |
| Patch size | 100 mcg/h patch size is 42 cm² of Duragesic ® patch size | | 54.6 | 24 |

Example 6

In vitro Skin Flux Study of Patch B2:

This study was designed to obtain in vitro transdermal flux data.

Results

Figure 11:
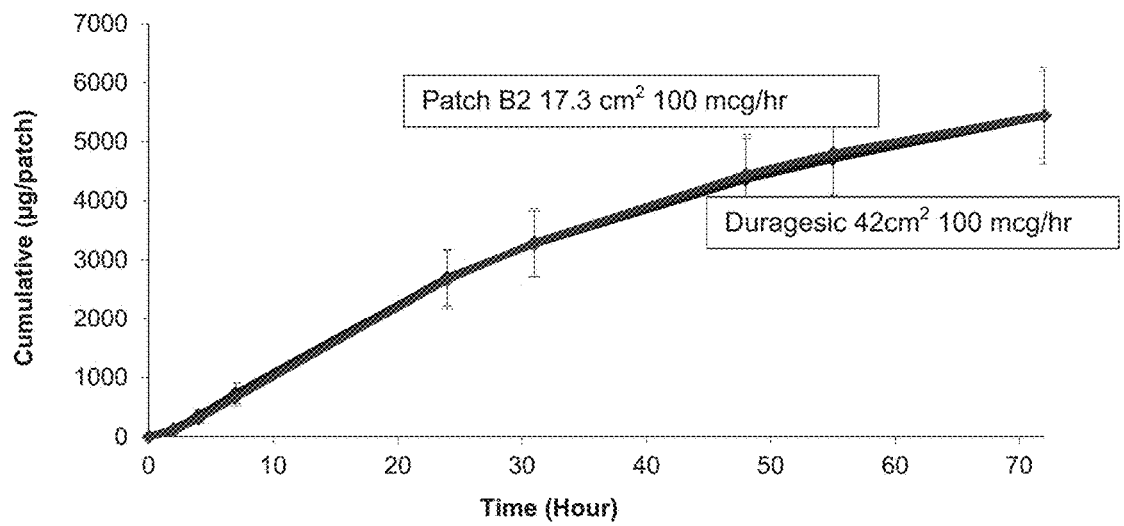
FIGS. 11 and 12 are line graphs showing the cumulative [μg/patch] and skin flux profile [μg/patch/hr] of Patch B2 versus the Duragesic® patch.
Figure 12:
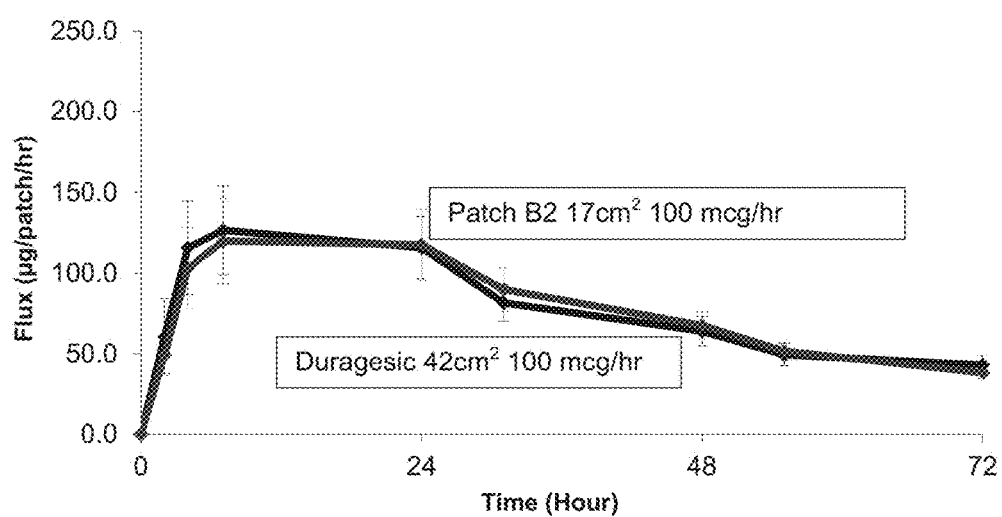
Figure 13:
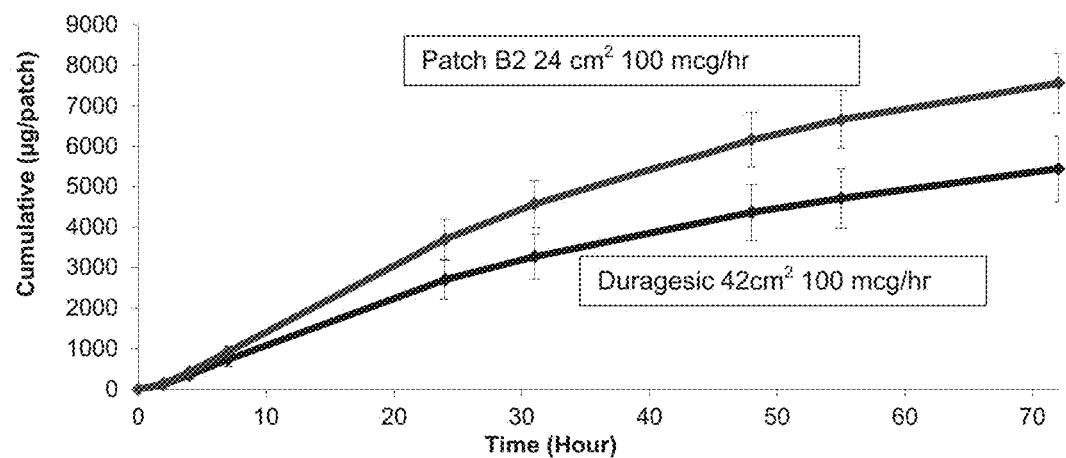
FIG. 13 is a line graph of showing in vitro delivery of a Patch B2 24 $cm^2$ 100 mcg/h central strip versus a 42 $cm^2$ 100 mcg/h Duragesic® patch.
Figure 14:
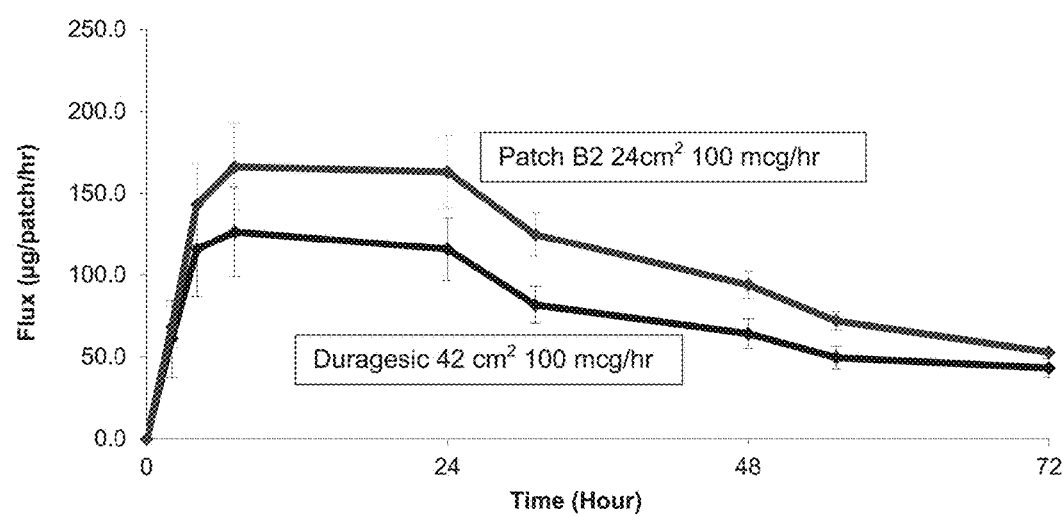
FIG. 14 is a line graph showing the in vitro fentanyl skin flux [μg/patch/hr] from Patch B2 24 $cm^2$ 100 mcg/h versus a 100 mcg/h Duragesic® patch.

FIGS. 10-14 show that the patches prepared by Example 5 deliver more fentanyl per cm² active patch than Duragesic® fentanyl transdermal system based on in vitro skin flux study experiments using modified Franz cell and human cadaver epidermis. Transdermal delivery is proportional to patch size. As shown in FIG. 10, 72 hour of in vitro cumulative delivery per cm² of Patch B2 17.3 cm² 100 mcg/h central strip is greater than the 42 cm² 100 mcg/h Duragesic® patch. FIGS. 11 and 12 show the cumulative [μg/patch] and skin flux profile [μg/patch/hr] of the Patch B2 17.3 cm² 100 mcg/h central strip matches that of the 42 cm² 100 mcg/h Duragesic® patch. FIG. 13 shows a Patch B2 24 cm² 100 mcg/h central strip delivers more fentanyl [in μg/patch] than the 42 cm² 100 mcg/h Duragesic® patch in vitro. FIG. 14 shows the in vitro fentanyl skin flux [μg/patch/hr] from Patch B2 24 cm² 100 mcg/h is higher than the 100 mcg/h Duragesic® patch.

Example 7

In Vitro Skin Buccal Flux Study

Method

Figure 16:
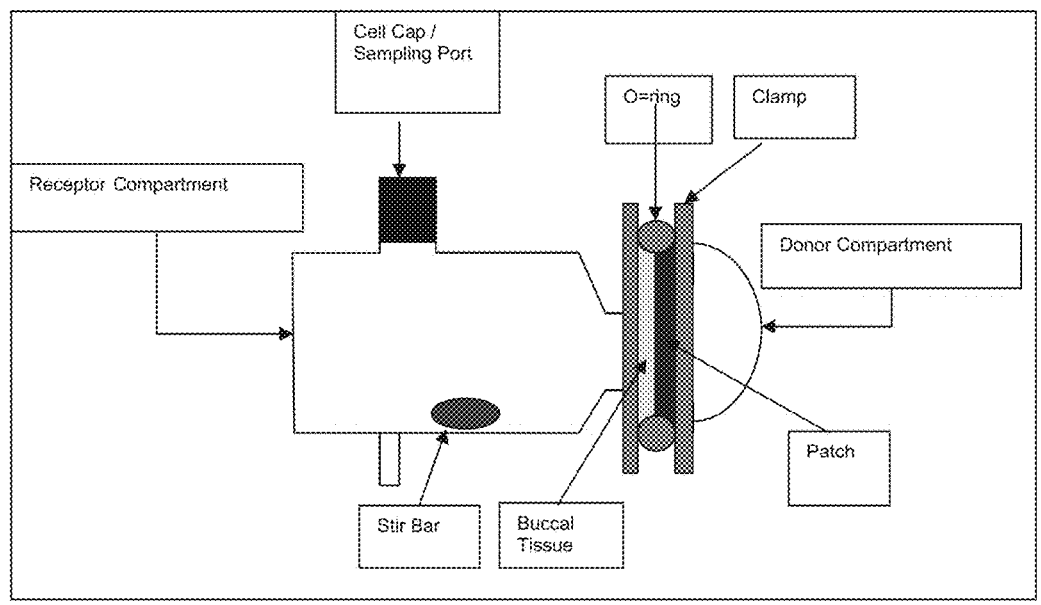
FIG. 16 is a schematic of an in vitro permeation study set-up.

With reference to FIG. 16, transbuccal delivery was simulated by permeation of naltrexone and fentanyl from a section of patch through human cadaver buccal tissue of 500 μm in thickness into the receptor solution, which is pH 6.8 commercially available artificial saliva stirred at 300 rpm at 37° C. The receptor fluid was stirred by means of a magnetic stirrer throughout the experiment to assure a uniform sample and a reduced diffusion barrier on the dermal side of the skin. The entire volume of receptor fluid was withdrawn at specified time intervals (0.25, 0.5, 1.0, 1.5, 2, 2.5, 3, 4, 7, and 24 hours) and immediately replaced with fresh fluid. The withdrawn fluid was filtered through a 0.45 μm filter. The last 1-2 mL was then analyzed for the active agent, e.g., fentanyl, using conventional high performance liquid chromatography methods. The cumulative amount of fentanyl penetrating through the cadaver buccal was calculated and reported as mcg/cm². Unless noted, the results are mean of 6 donors, 1 replicate per donor for Patch B2 while reference product Duragesic® calculations are mean of 18 donors, 1 or 2 replicates per donor.

Because the impermeable polyester barrier between skin contact layer and the non-skin contact layer of the patch prevents permeation through the buccal tissue in this in vitro test system, each side of the patch (skin contact layer and non-skin contact layer) was tested separately in this model in order to evaluate the conditions of human oral use, where both layers would be in contact with oral tissue.

Permeation through skin contact layer—To assess buccal permeation of fentanyl and naltrexone from Duragesic® and Patch B2 skin contact layer, a 7 cm² die cut of the fentanyl and naltrexone HCl skin contact strip was applied to a 500 μm thick buccal cell. The patch-buccal tissue was then assembled to a modified Franz donor cell with the buccal tissue in contact with the receptor solution.

Permeation through non-skin contact layer—To assess buccal permeation of naltrexone from the non-skin contact layer, the semipermeable backing film side of the non-skin contact layer was applied to buccal tissue and then assembled to a modified Franz cell with the buccal tissue in contact with the receptor solution.

Results

Figure 17:
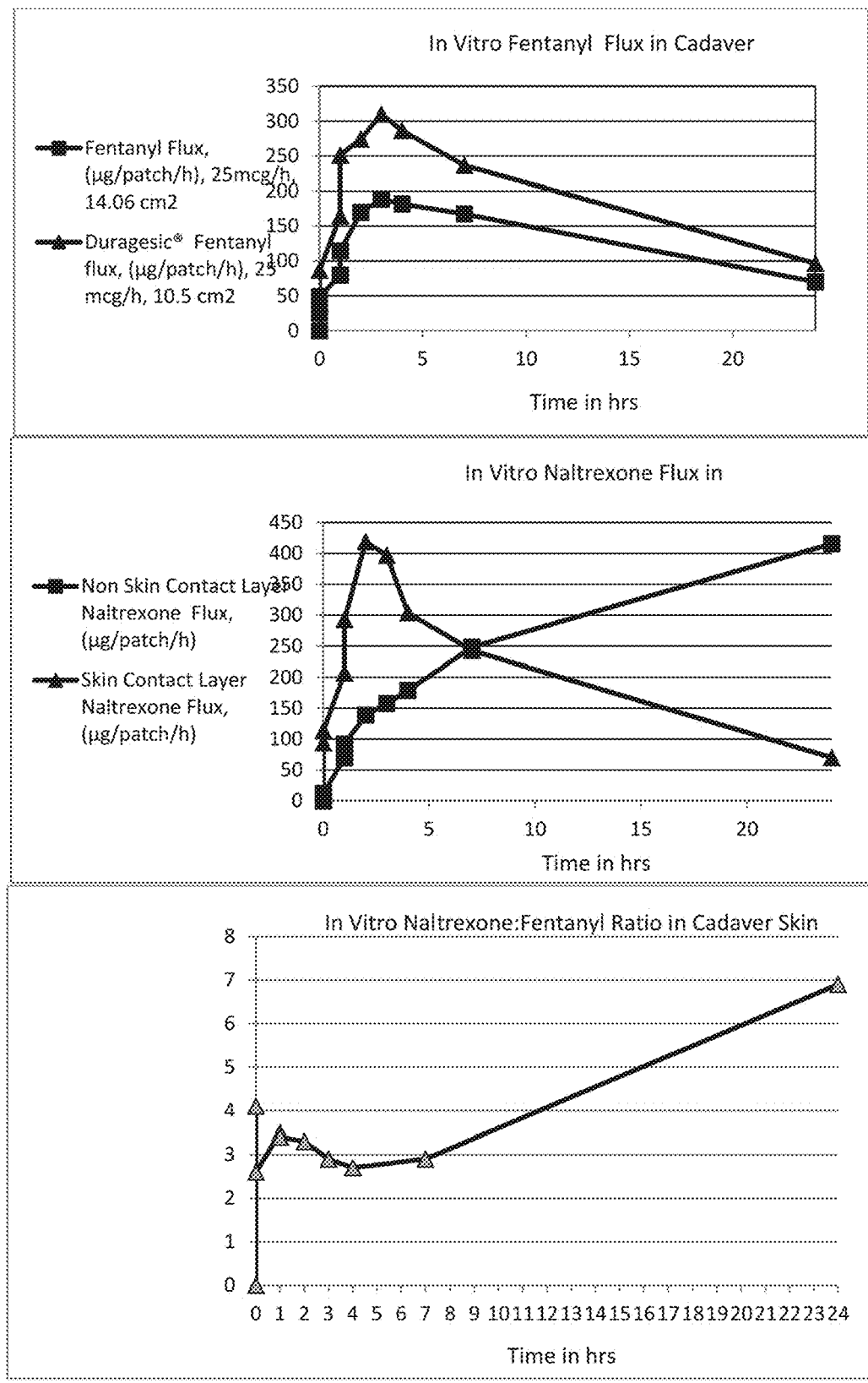
FIG. 17 is a line graph showing the transbuccal delivery rate of fentanyl from Patch B2 as compared to the Duragesic® patch.

As illustrated in FIG. 17, the transbuccal delivery rate of fentanyl from Patch B2 was comparable to the reference product Duragesic®. The transbuccal delivery rate of naltrexone in the non-skin contact layer and that of naltrexone in the skin contact layer are listed in the Table 5. The Patch B2 non-skin contact layer provides additional naltrexone transbuccal delivery. The total combined transbuccal delivery rate of naltrexone from Patch B2 from the 2 layers is thus even higher than the fentanyl delivery rate from the Patch B2 patch. The ratio of naltrexone delivery to fentanyl delivery is 4.1 and 2.6 in the early time points (0.25 h, 0.5 h) and 3.5 to 6.3 in later time points (1 to 24 h).

TABLE 5

In Vitro Naltrexone and Fentanyl Buccal Delivery Rate of Patch B2 using Human Cadaver Buccal Tissue

| Time Point (h) | Non Skin Contact Layer Naltrexone Flux (μg/patch/h) | Skin Contact Layer Naltrexone Flux (μg/patch/h) | Total Naltrexone Flux (μg/patch/h) | Fentanyl Flux, (μg/patch/h), 25 mcg/h 14.06 cm² | Duragesic® Fentanyl flux, (μg/patch/h), 25 mcg/h, 10.5 cm² | Naltrexone/ Fentanyl Ratio |
|---|---|---|---|---|---|---|
| 0.00 | 0.0 | 0.0 | 0.0 | 0.0 | 0.0 | 0.0 |
| 0.25 | 9.0 | 93.7 | 102.7 | 25.3 | 38.3 | 4.1 |
| 0.50 | 12.1 | 113.6 | 125.7 | 48.9 | 86.7 | 2.6 |
| 1.00 | 69.3 | 207.0 | 276.3 | 79.6 | 164.5 | 3.5 |
| 1.50 | 92.1 | 292.7 | 384.8 | 114.5 | 251.2 | 3.4 |
| 2.00 | 138.8 | 418.8 | 557.5 | 169.6 | 274.1 | 3.3 |
| 3.00 | 157.5 | 396.7 | 554.2 | 188.9 | 309.8 | 2.9 |
| 4.00 | 178.7 | 303.7 | 482.5 | 181.7 | 286.4 | 2.7 |
| 7.00 | 248.1 | 242.8 | 490.9 | 167.5 | 236.6 | 2.9 |
| 24.00 | 415.7 | 69.8 | 485.5 | 70.0 | 96.5 | 6.9 |

Example 8

Solvent Extraction Method

Patch B2, 25 mcg/h strength is cut into halves. The liner from each half is peeled off. Both halves are transferred into a 20-mL glass vial. Ten mL of appropriate extraction medium is pipetted into the glass vial with screw cap. The vial was shaken for 2 hours at 180 osc/minute at room temperature or at 125 strike/minute in 70° C. water bath. Samples (20 μL) are pipetted into separated HPLC vials at time points of 10 min, 30 min and 120 min, and diluted with 980 μL of Diluent for analysis by HPLC. Extraction media were DI Water, Ethanol, Cooking Vinegar, pH 6.8 phosphate buffer and artificial saliva (Dissolve 16 g of sodium chloride, 0.38 g of sodium phosphate monobasic and 4.76 g of sodium phosphate dibasic into 2000 mL of water. Adjust pH to 6.8 with sodium hydroxide. Mix well and filter the solution through a 0.45-μm membrane filter. Degas the solution for 15 minutes.

Figure 18:
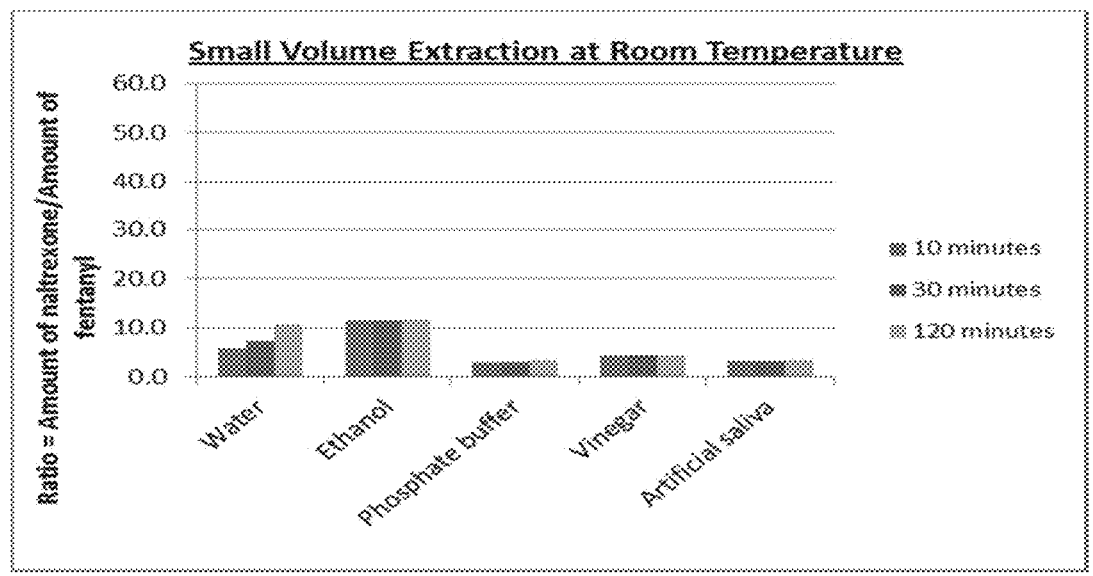
FIG. 18 is a bar graph showing the extraction of fentanyl and naltrexone from cut Patch B2 (14.06 $cm^2$; 25 mcg/h) at room temperature using water, ethanol, phosphate buffer, vinegar, and artificial saliva.
Figure 19:
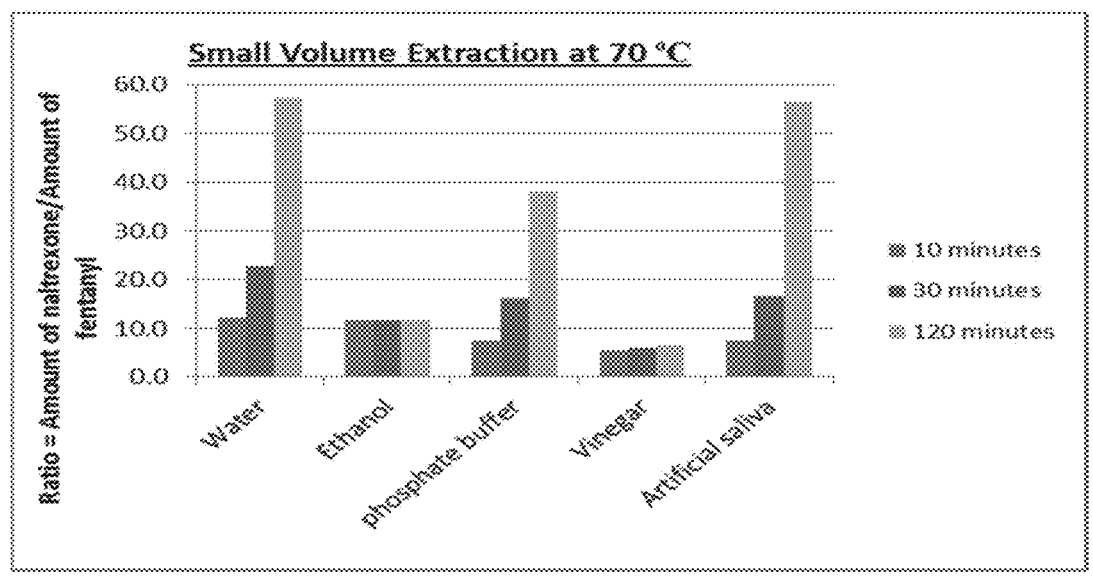
FIG. 19 is a bar graph showing the extraction of fentanyl and naltrexone from cut Patch B2 (14.06 $cm^2$; 25 mcg/h) at 70° C. using water, ethanol, phosphate buffer, vinegar, and artificial saliva.

FIG. 18 shows the simulated small volume solvent extraction from cut Patch B2 (14.06 cm²; 25 mcg/h) at room temperature. FIG. 19 shows the simulated small volume solvent extraction from cut Patch B2 (14.06 cm²; 25 mcg/h Patch) at 70° C.

TABLE 6

Simulated Small Volume Solvent Extraction from Cut Patch B2 (14.06 cm² 25 mcg/h Patch)

| Solvent | T | Sampling Time Point (min) | Fentanyl Base Theoretical Value: 2.52 mg | | Naltrexone Base Theoretical Value: 29.299 mg | | Ratio (Wt$_{Naltrexone}$/ Wt$_{Fentanyl}$) Avg. of 2 |
|---|---|---|---|---|---|---|---|
| | | | Amount Dissolved (mg) Avg. of 2 | Dissolved (% LC) Avg. of 2 | Amount Dissolved (mg) Avg. of 2 | Dissolved (% LC) Avg. of 2 | |
| Water | RT | 10 | 0.32 | 12.8 | 1.90 | 6.5 | 5.9 |
| | | 30 | 0.34 | 13.3 | 2.41 | 8.2 | 7.2 |
| | | 120 | 0.32 | 12.6 | 3.45 | 11.8 | 10.9 |
| | 70° C. | 10 | 0.38 | 15.3 | 4.71 | 16.1 | 12.2 |
| | | 30 | 0.27 | 10.8 | 6.17 | 21.1 | 22.8 |
| | | 120 | 0.16 | 6.4 | 9.29 | 31.7 | 57.3 |
| Ethanol | RT | 10 | 1.87 | 74.2 | 21.46 | 73.2 | 11.5 |
| | | 30 | 1.77 | 70.4 | 20.58 | 70.2 | 11.6 |
| | | 120 | 1.79 | 71.2 | 20.94 | 71.5 | 11.7 |
| | 70° C. | 10 | 1.89 | 74.9 | 22.19 | 75.7 | 11.7 |
| | | 30 | 2.02 | 80.2 | 23.97 | 81.8 | 11.9 |
| | | 120 | 1.90 | 75.3 | 22.51 | 76.8 | 11.9 |
| pH 6.8 Phosphate Buffer | RT | 10 | 0.94 | 37.2 | 2.75 | 9.4 | 2.9 |
| | | 30 | 1.16 | 46.2 | 3.46 | 11.8 | 3.0 |
| | | 120 | 1.29 | 51.0 | 4.57 | 15.6 | 3.6 |
| | 70° C. | 10 | 0.85 | 33.6 | 6.40 | 21.8 | 7.6 |
| | | 30 | 0.63 | 25.1 | 10.32 | 35.2 | 16.3 |
| | | 120 | 0.43 | 16.9 | 16.29 | 55.6 | 38.1 |
| Cooking Vinegar | RT | 10 | 0.48 | 19.2 | 2.17 | 7.4 | 4.5 |
| | | 30 | 0.59 | 23.6 | 2.60 | 8.9 | 4.4 |
| | | 120 | 0.68 | 26.9 | 2.95 | 10.1 | 4.3 |

TABLE 6-continued

Simulated Small Volume Solvent Extraction from Cut Patch B2 (14.06 cm² 25 mcg/h Patch)

| Solvent | T | Sampling Time Point (min) | Fentanyl Base Theoretical Value: 2.52 mg | | Naltrexone Base Theoretical Value: 29.299 mg | | Ratio (Wt$_{Naltrexone}$/ Wt$_{Fentanyl}$) Avg. of 2 |
|---|---|---|---|---|---|---|---|
| | | | Amount Dissolved (mg) Avg. of 2 | Dissolved (% LC) Avg. of 2 | Amount Dissolved (mg) Avg. of 2 | Dissolved (% LC) Avg. of 2 | |
| | 70° C. | 10 | 0.52 | 20.8 | 2.96 | 10.1 | 5.7 |
| | | 30 | 0.74 | 29.4 | 4.50 | 15.3 | 6.1 |
| | | 120 | 1.02 | 40.7 | 6.80 | 23.2 | 6.6 |
| Artificial Saliva | RT | 10 | 0.70 | 27.6 | 2.24 | 7.6 | 3.2 |
| | | 30 | 0.90 | 35.7 | 2.90 | 9.9 | 3.2 |
| | | 120 | 1.07 | 42.6 | 3.87 | 13.2 | 3.6 |
| | 70° C. | 10 | 0.71 | 28.0 | 5.25 | 17.9 | 7.4 |
| | | 30 | 0.50 | 19.8 | 8.33 | 28.4 | 16.7 |
| | | 120 | 0.23 | 8.9 | 12.73 | 43.4 | 56.5 |

Abbreviations: % LC = percent of label claim (percent of the amount in the patch claimed by the prescribing information); HCl = hydrochloride; Wt$_{Naltrexone}$ = Weight of Naltrexone extracted from the Patch, Wt$_{Fentanyl}$ = Weight of Fentanyl extracted from the Patch; min = minute Those skilled in the art will appreciate that numerous changes and modifications can be made to the preferred embodiments of the disclosure and that such changes and modifications can be made without departing from the spirit of the disclosure. It is, therefore, intended that the appended claims cover all such equivalent variations as fall within the true spirit and scope of the disclosure.

What is claimed is:

1. A transdermal dosage system for administering fentanyl to a human, the system having reduced potential for abuse and comprising:
    a first antagonist reservoir comprising fentanyl, or a pharmaceutically acceptable salt thereof, and naltrexone, or a pharmaceutically acceptable salt thereof; and
    a second antagonist reservoir comprising naltrexone, or a pharmaceutically acceptable salt thereof;
    wherein the first and second antagonist reservoirs are separated from each other by a barrier that is impermeable to the fentanyl, or the pharmaceutically acceptable salt thereof, and the naltrexone, or the pharmaceutically acceptable salt thereof; and
    wherein the ratio of naltrexone, or a pharmaceutically acceptable salt thereof, to fentanyl, or a pharmaceutically acceptable salt thereof, extracted from the system when the system is tampered with is at least 1:1.

2. The transdermal dosage system of claim 1, wherein the tampering comprises immersion or substantial immersion of the system in a solvent.

3. The transdermal dosage system of claim 2, wherein the solvent is an aqueous solvent or an organic solvent.

4. The transdermal dosage system of claim 2, wherein the solvent is water.

5. The transdermal system of claim 4, wherein the ratio of the naltrexone, or a pharmaceutically acceptable salt thereof, to the fentanyl, or a pharmaceutically acceptable salt thereof, extracted from the dosage form at room temperature is at least 3.4:1 after 10 minutes of tampering.

6. The transdermal system of claim 4, wherein the ratio of the naltrexone, or a pharmaceutically acceptable salt thereof, to the fentanyl, or a pharmaceutically acceptable salt thereof, extracted from the dosage form at 70° C. is at least 4.8:1 after 10 minutes of tampering.

7. The transdermal system of claim 4, wherein the ratio of the naltrexone, or a pharmaceutically acceptable salt thereof, to the fentanyl, or a pharmaceutically acceptable salt thereof, extracted from the dosage form at 70° C. is at least 6.6:1 after 30 minutes of tampering.

8. The transdermal system of claim 4, wherein the ratio of the naltrexone, or a pharmaceutically acceptable salt thereof, to the fentanyl, or a pharmaceutically acceptable salt thereof, extracted from the dosage form at room temperature is at least 3.6:1 after 30 minutes of tampering.

9. The transdermal dosage system of claim 3, wherein the aqueous solvent is cooking vinegar.

10. The transdermal system of claim 9, wherein the ratio of the naltrexone, or a pharmaceutically acceptable salt thereof, to the fentanyl, or a pharmaceutically acceptable salt thereof, extracted from the dosage form at room temperature is at least 5.4:1 after 10 minutes of tampering.

11. The transdermal system of claim 9, wherein the ratio of the naltrexone, or a pharmaceutically acceptable salt thereof, to the fentanyl, or a pharmaceutically acceptable salt thereof, extracted from the dosage form at 70° C. is at least 4.6:1 after 10 minutes of tampering.

12. The transdermal system of claim 9, wherein the ratio of the naltrexone, or a pharmaceutically acceptable salt thereof, to the fentanyl, or a pharmaceutically acceptable salt thereof, extracted from the dosage form at 70° C. is at least 4.9:1 after 30 minutes of tampering.

13. The transdermal system of claim 9, wherein the ratio of the naltrexone, or a pharmaceutically acceptable salt thereof, to the fentanyl, or a pharmaceutically acceptable salt thereof, extracted from the dosage form at room temperature is at least 5.2:1 after 30 minutes of tampering.

14. The transdermal dosage system of claim 3, wherein the organic solvent is ethanol.

15. The transdermal system of claim 14, wherein the ratio of the naltrexone, or a pharmaceutically acceptable salt thereof, to the fentanyl, or a pharmaceutically acceptable salt thereof, extracted from the dosage form at room temperature is at least 5.9:1 after 10 minutes of tampering.

16. The transdermal system of claim 14, wherein the ratio of the naltrexone, or a pharmaceutically acceptable salt thereof, to the fentanyl, or a pharmaceutically acceptable salt thereof, extracted from the dosage form at 70° C. is at least 5.9:1 after 10 minutes of tampering.

17. The transdermal system of claim 14, wherein the ratio of the naltrexone, or a pharmaceutically acceptable salt thereof, to the fentanyl, or a pharmaceutically acceptable salt thereof, extracted from the dosage form at 70° C. is at least 6.0:1 after 30 minutes of tampering.

18. The transdermal system of claim 14, wherein the ratio of the naltrexone, or a pharmaceutically acceptable salt thereof, to the fentanyl, or a pharmaceutically acceptable salt thereof, extracted from the dosage form at room temperature is at least 6.0:1 after 30 minutes of tampering.

19. The transdermal dosage system of claim 3, wherein the aqueous solvent is pH 6.8 phosphate buffer.

20. The transdermal dosage system of claim 2, wherein the solvent is artificial saliva.

21. The transdermal dosage system of claim 1, wherein the ratio of the naltrexone, or a pharmaceutically acceptable salt thereof, to the fentanyl, or a pharmaceutically acceptable salt thereof, extracted from the dosage system by each of water, ethanol, pH 6.8 phosphate buffer, cooking vinegar, or artificial saliva, is at least 1:1 after between 5 minutes and 4 hours of tampering.

22. The transdermal dosage system of claim 1, wherein the tampering occurs at room temperature.

23. The transdermal dosage system of claim 1, wherein the tampering occurs at 70° C.

24. The transdermal dosage system of claim 1, wherein the ratio of the naltrexone, or a pharmaceutically acceptable salt thereof, to the fentanyl, or a pharmaceutically acceptable salt thereof, extracted from the dosage form at room temperature after 10 minutes of tampering is
    at least 3.4:1 when the tampering comprises water and
    at least 5.9:1 when the tampering comprises ethanol.

25. The transdermal dosage system of claim 1, wherein the ratio of the naltrexone, or a pharmaceutically acceptable salt thereof, to the fentanyl, or a pharmaceutically acceptable salt thereof, extracted from the dosage form at 70° C. after 10 minutes of tampering is
    at least 4.8:1 when the tampering comprises water and
    at least 5.9:1 when the tapering comprises ethanol.

26. The transdermal dosage system of claim 1, wherein the ratio of the naltrexone, or a pharmaceutically acceptable salt thereof, to the fentanyl, or a pharmaceutically acceptable salt thereof, extracted from the dosage form at room temperature after 30 minutes of tampering is
    at least 3.6:1 when the tampering comprises water and
    at least 6.0:1 when the tampering comprises ethanol.

27. The transdermal dosage system of claim 1, wherein the ratio of the naltrexone, or a pharmaceutically acceptable salt thereof, to the fentanyl, or a pharmaceutically acceptable salt thereof, extracted from the dosage form at 70° C. after 30 minutes of tampering is
    at least 6.6:1 when the tampering comprises water and
    at least 6.0:1 when the tampering comprises ethanol.

* * * * *